US006791089B1

(12) United States Patent
Caffrey et al.

(10) Patent No.: US 6,791,089 B1
(45) Date of Patent: Sep. 14, 2004

(54) PINS CHEMICAL IDENTIFICATION SOFTWARE

(75) Inventors: Augustine J. Caffrey, Idaho Falls, ID (US); Kennth M. Krebs, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/537,906

(22) Filed: Mar. 28, 2000

Related U.S. Application Data
(60) Provisional application No. 60/126,698, filed on Mar. 29, 1999.

(51) Int. Cl.$^7$ .......................................... G01N 23/222
(52) U.S. Cl. .................................................. 250/358.1
(58) Field of Search ..................... 250/358.1; 376/159; 702/28

(56) References Cited

U.S. PATENT DOCUMENTS

| | | | | |
|---|---|---|---|---|
| 3,739,171 A | * | 6/1973 | Scott ........................ | 250/269.6 |
| 3,778,627 A | * | 12/1973 | Carpenter .................... | 376/192 |
| 3,832,545 A | | 8/1974 | Bartko ........................ | 376/159 |
| 4,190,768 A | * | 2/1980 | Arnold et al. .............. | 376/159 |

(List continued on next page.)

OTHER PUBLICATIONS

Alvarez, R.A., et al., "Toole NDE Test Report LLNL 14–MeV Neutron Activation Group", Lawrence Livermore National Laboratory, Livermore, CA (reproduced by U.S. Department of Commerce, National Technical Information Service, Springfield, VA), pp. 1–27 (Jun. 1991).

Bach, P., et al., "Chemical weapons detection by fast neutron activation analysis techniques", *Nuclear Instruments and Methods In Physics Research*, B79, pp. 605–610 North–Holland (1993).

Rhodes, E., et al., "APSTNG: Neutron Interrogation for Detection of Nuclear and CW Weapons, Explosives, and Drugs", 4$^{th}$ World Neutron Radiography Conf., San Francisco, CA, pp. 827–835 (May 11–14, 1992).

Rhodes, E., et al., "APSTNG: Neutron Interrogation of Explosives and Drugs and Nuclear and CW Materials", submitted to SPIE 1992 International Symposium on Optical Applied Science and Engineering, San Diego, CA, pp. 1–11 (Jul. 19–24, 1992).

Rhodes, E., et al., "ASPTNG: Radiation Interrogation for Verification of Chemical and Nuclear Weapons", *IEEE Transactions on Nuclear Science*, vol. 39, No. 4 pp. 1041–1045 (1992).

Taylor, T.T., "An Assessment of Nondestructive Testing Technologies For Chemical Weapons Monitoring", prepared for the U.S. Department of Energy Office of Arms Control and Nonproliferation and the Defense Nuclear Agency Office of Arms Control and Test Limitations under Contract DE–AC06–76RLO 1830, pp. 16–21, Appendixes D and E (May 1993).

*Primary Examiner*—Constantine Hannaher
*Assistant Examiner*—Shun Lee
(74) *Attorney, Agent, or Firm*—Klaas Law O'Meara & Malkin

(57) ABSTRACT

An apparatus and method for identifying a chemical compound. A neutron source delivers neutrons into the chemical compound. The nuclei of chemical elements constituting the chemical compound emit gamma rays upon interaction with the neutrons. The gamma rays are characteristic of the chemical elements constituting the chemical compound. A spectrum of the gamma rays is generated having a detection count and an energy scale. The energy scale is calibrated by comparing peaks in the spectrum to energies of pre-selected chemical elements in the spectrum. A least-squares fit completes the calibration. The chemical elements constituting the chemical compound can be readily determined, which then allows for identification of the chemical compound.

24 Claims, 24 Drawing Sheets

U.S. PATENT DOCUMENTS

| | | | |
|---|---|---|---|
| 4,278,885 A | * 7/1981 | von Alfthan et al. | 250/370.01 |
| 4,882,121 A | 11/1989 | Grenier | 376/159 |
| 4,918,315 A | 4/1990 | Gomberg et al. | 250/390.04 |
| 5,076,993 A | 12/1991 | Sawa et al. | 376/159 |
| 5,098,640 A | 3/1992 | Gozani et al. | 376/166 |
| 5,162,096 A | 11/1992 | Gozani | 376/159 |
| 5,200,626 A | 4/1993 | Schultz et al. | 250/390.04 |
| 5,340,990 A | * 8/1994 | Brackenbush et al. | 250/395 |
| 5,378,895 A | 1/1995 | Cole et al. | 250/390.04 |
| 5,838,759 A | * 11/1998 | Armistead | 378/57 |
| 5,982,838 A | * 11/1999 | Vourvopoulos | 376/159 |

\* cited by examiner

PINS CHEMICAL IDENTIFICATION SOFTWARE

This application claims the benefit of U.S. Provisional Application No. 60/126,698, for PINS CHEMICAL IDENTIFICATION SOFTWARE filed Mar. 29, 1999, which is hereby incorporated by reference for all that is disclosed therein.

CONTRACTUAL ORIGIN OF THE INVENTION

This invention was made with United States Government support under Contract No. DE-AC07-94ID13223, now Contract No. DE-AC07-99ID13727, awarded by the United States Department of Energy. The United States Government has certain rights in the invention.

FIELD OF THE INVENTION

This invention relates to a method and apparatus for the non-destructive identification of chemicals using prompt gamma-ray neutron activation analysis. More particularly, the invention relates to non-destructive testing to identify chemicals stored in sealed containers using a portable, field deployable, isotopic, neutron bombardment, spectroscopic method and apparatus.

The invention has particular application for the identification of military chemical warfare agents located in sealed munitions. Munitions are irradiated with neutrons and the resultant prompt gamma-ray emission spectra are analyzed to reveal the chemical elements comprising the agent. The identity of the agent may then be readily determined.

The method and apparatus have further application to any situation requiring the identification of other unknown chemicals. For example, the invention could be used in airports to examine cargo or luggage. Likewise, it could be deployed to non-invasively test for hazardous or contraband materials in containerized cargo or other sealed shipping containers. The invention is also useful for identifying suspected clandestine munitions manufacturing or storage facilities.

BACKGROUND OF THE INVENTION

This invention was made in the course of developing a safe, non-destructive, and portable method and apparatus for determining the contents of sealed military munitions and containers. Every year the United States military recovers a large number of munitions from the field. Most of these munitions are recovered from disposal areas, firing ranges, active and formerly active military installations, and defense munition stockpile sites.

These munitions are typically unexploded bombs, projectiles, and containers, which can be extremely dangerous. Their fuses may be armed and their casings may be fragile from corrosion and the shock of firing and landing. They may contain explosives, military obscuring smokes, practice fills, or chemical warfare agents, such as nerve agents.

The United States military identifies munition fills in bombs and projectiles by a color code, a description stenciled on each item, and lot numbers stamped in the shell casings. However, unexploded munitions may have been buried or exposed to the elements for years before they are recovered. Often, the identifying marks are obscured or obliterated by rust, abrasion, corrosion or other deterioration. The safe and lawful disposal of munitions requires that their contents be determined prior to disposal, which can be difficult when the above-listed identifying marks are not readily visible.

Currently, munitions in which the fill cannot be readily determined are initially assessed by military explosive ordinance disposal and chemical weapons experts. After initial visual examination, an expert places the munition in an airtight steel container or overpack to protect against leaks of the chemical fill. The munition is then radiographed to determine the location of internal components. After being radiographed, the munition is assessed by a neutron activation analysis technique known as portable isotopic neutron spectroscopy (sometimes referred to simply as "PINS").

The United States military has used the PINS system for non-destructive identification of suspect chemical munitions and containers for several years. The contents of items analyzed by PINS have varied from muddy water and sand to chemical warfare agents including the nerve agent sarin, mustard gas, lewisite, and blood agents. The PINS system employs neutron radiation to probe the chemical elements within a sealed munition or container. The output of the PINS assay is in the form of uncalibrated, raw gamma-ray spectra from a portable high-purity germanium gamma-ray spectrometer. The process of generating the gamma-ray spectra is usually performed in the field, i.e., at a munitions disposal site. These gamma-ray spectra are then sent to a nuclear laboratory for expert interpretation to identify the contents of the container or munition.

The data produced by the portable isotopic neutron spectroscopy method has to be analyzed in the laboratory by highly skilled and experienced scientists and engineers to correctly assess whether any dangerous chemicals are present in the containers or munitions. This requirement for such specialized personnel often seriously extends the period between examination of a munition and its disposal. In addition, human judgment errors regarding the contents of a chemical warfare munition are possible and may result in improper handling or disposal of the chemical warfare munition.

Accordingly, prior to development of the present invention, there had been a long-felt need for a portable isotopic neutron spectroscopy method and apparatus that could be operated in the field by persons not having extensive scientific and technical knowledge of physics and chemistry.

SUMMARY OF THE INVENTION

A method and apparatus for quickly determining the chemical composition of a chemical agent in a container are provided. The method involves exposing the agent to neutrons that excite the atomic nuclei of the agent to produce gamma-ray emissions. A radiation detector senses the gamma-ray emissions generated by the agent and outputs data that is representative of the energy levels of the emissions. The data is typically in the form of voltage pulses that are representative of the energy of the gamma rays. The data is then processed by a multichannel analyzer, which generates a spectrum of the gamma-ray emissions. The gamma-ray spectrum is automatically energy-calibrated and analyzed to identify the chemical elements that are present in the agent. The relative amounts of the chemical elements present in the agent are also determined.

Based on the chemical elements comprising the agent, the chemical compound or mixture of the agent is assessed via a decision tree algorithm. A decision tree algorithm is executed, wherein the relative amounts of the chemical elements in the agent are compared to a look up table of chemical compositions with known relative amounts of the same chemical elements. When a match is made between the chemical elements of the agent and the table, the match is reported by a computer in an easily readable format that identifies the agent in plain language for the operator.

Analysis of the gamma-ray spectral data begins with calibrating the energy scale of the spectrum. The voltage of each pulse arriving at the multichannel analyzer is proportional to the ionization energy deposited in the sensitive volume of the detector. After amplification and reshaping, the multichannel amplifier sorts each pulse according to its voltage into a histogram bin or "channel." The number of pulses or "counts" per channel represents the gamma-ray intensity at a given energy level. A complete gamma-ray spectrum typically has 4,096 to 16,384 channels and is similar to a graph of gamma-ray intensity on a y-axis versus channel and/or detector pulse-height voltage on an x-axis. The energy calibration procedure, in effect, rescales the x-axis in energy rather than voltage units, e.g., thousands of electron volts ("kiloelectron volts" or "keV" hereinafter). Energy calibration is necessary because the amplification factor or gain of the detector and the multichannel analyzer may change over time due to thermal or random effects.

The energy calibration of the spectroscopy system is derived from the positions of neutron-induced gamma rays or natural background radiation observed in most or all spectra recorded by the detector. Specifically, these include gamma rays produced by neutron interactions in the detector itself, neutron interactions in shielding materials surrounding the detector, and neutron interactions in the container or munition wall materials. For example, steel in a munition casing interacts with the neutrons and causes specific gamma-ray emissions, e.g., emissions representative of iron.

An energy calibration algorithm converts the x-axis scale from channels to kiloelectron volts using an expression of the form $E(i)=a+bi+ci^2$, where i is the channel number, $E(i)$ is the energy of the ith channel in keV, and a, b, and c are calibration constants to be determined by the algorithm.

To determine the calibration constants, the algorithm first searches the spectrum for peaks significantly above the background. The centroids of these peaks are matched to a specified pattern to identify the individual peaks. Then, a non-linear least square fit of experimental peak energies versus expected peak energies is performed to determine the three constants.

Once calibrated, the gamma-ray spectrum is direct reading. The spectrum is then searched for selected chemical elements by performing a directed peak fit of the corresponding gamma-ray energies. For those peaks detected at a significant level above the background, peak centroid energies and net peak areas are extracted from the spectrum to determine the gamma-ray counting rates for the chemical elements of interest.

A decision tree algorithm is then executed to identify the fill agent based on the chemical elements of which the fill agent is comprised. The decision tree first narrows the possible fill agent choices by the presence and absence of various chemical elements. For example, if phosphorus is detected in a munition under test, there are only two possible fills, white phosphorus smoke, or an organophosphorus nerve agent. The final step in the decision tree is to compare the gamma-ray count rates from selected chemical elements to determine the best match from the remaining possibilities. Continuing with the previous example, white phosphorus munitions typically contain 70–100 weight-% phosphorus and 0–3 weight-% hydrogen, while nerve agents normally contain 11–22 weight-% phosphorus and 7–10 weight-% hydrogen. The spectral gamma-ray counting rates faithfully reflect these ratios. Finally, the computer reports the identity of the fill agent to the system operator in an easily readable format.

DETAILED DESCRIPTION OF A PREFERRED EMBODIMENT

Figure 1:
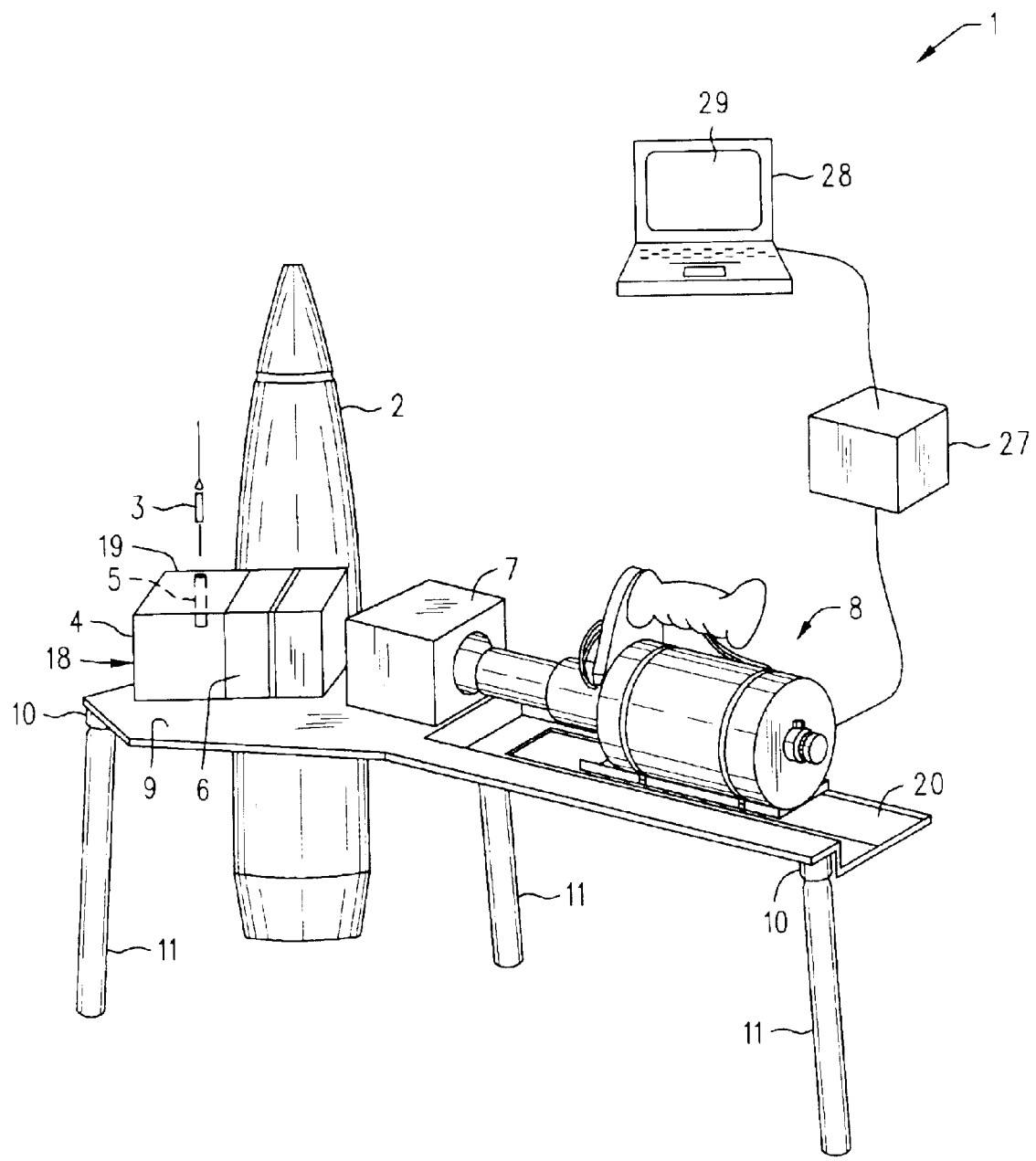
FIG. 1 is a schematic illustration of a portable isotopic neutron spectroscopy system configured to identify a fill agent within an artillery shell.

FIG. 1 is a schematic illustration of a portable prompt gamma-ray neutron activation analysis system 1 (sometimes referred to herein simply as the "system"). The system 1 is configured to assay a chemical fill (not shown in FIG. 1 and shall be considered representative only of a non-limiting example). The chemical fill (sometimes referred to as an ("agent") is shown located inside a munition 2. For illustration purposes, the munition 2 is depicted as a military artillery shell. However, it should be understood that the munition 2 may be any container having an agent located therein.

In a non-limiting embodiment of the system 1, the system 1 has a neutron-emitting assembly 18, located in the proximity of the munition 2. The neutron generator 18 has a moderator block 4 placed adjacent a tungsten shadow shield 6. A neutron source 3 of energetic neutrons is shown above the moderator block 4. The neutron source 3 may, as an example, comprise californium-252 and moderator block 4 may, as an example, be comprised of polyethylene. During operation of the system 1, the neutron source 3 is located within a slot 5 located within the moderator block 4. The moderator block 4 has a side 19 that faces the munition 2. In a non-limiting embodiment of the neutron-emitting assembly 18, the slot 5 is located on the side 19 of the moderator block 4.

The placement of the slot 5 in close proximity to the side 19 provides for a flux of both fast neutrons and slow neutrons on the munition 2. The source 3 emits fast neutrons with equal likelihood in all directions. Neutrons emitted away from munition 2 suffer multiple elastic scattering on the hydrogen nuclei inside the moderator block 4, often reducing their kinetic energy by a factor of one million. Many of these "slow" or "thermal" neutrons are redirected toward munition 2. Neutrons emitted by the source 3 toward the munition 2 encounter little or no moderator, and hence, their energies are not diminished before they arrive at munition 2. These neutrons are commonly termed "fast" neutrons. Fast and slow neutrons play complimentary roles in the excitation of the fill chemical inside the munition. Some chemical elements, e.g., phosphorus, are excited more efficiently by fast neutron inelastic scattering, while others, for example hydrogen and chlorine, are more efficiently excited by capture of slow neutrons. The geometric arrangement of placing the source 3 between of the moderator block 4 and the munition 2 has the effect of redirecting neutrons that otherwise would be lost back toward the munition 2.

A bismuth collimator 7 and a detector 8 (both of standard design) are also located in the proximity of the munition 2. The collimator 7 serves to limit extraneous gamma rays from being detected by the detector 8. The detector 8 may, as an example, be of the type known as a high purity germanium detector (HPGe) and may be an Ortec, model GMX detector. The detector 8 serves to detect gamma rays and outputs data corresponding to the energy levels of the detected gamma rays. The detector 8 is electrically connected to a multichannel analyzer 27 (also of conventional design). The multichannel analyzer 27 sorts the energies of the gamma rays into channels and counts the number of gamma rays that are in each channel. The multichannel analyzer 27 may, as an example, be an Ortec Nomad Plus multichannel. These data from the multichannel analyzer are output to a computer 28, e.g., a notebook computer, that displays and analyzes the data.

In a non-limiting embodiment of the system 1, the moderator block 4, the shadow shield 6, the collimator 7, and the detector 8 are all placed above the ground on a table 9, which is supported by legs 11. The table 9 and the legs 11 may, as an example, be comprised of aluminum or steel.

The system 1 is designed for field assessment of a wide variety of munitions 2. It is important to install the neutron generator 18, the collimator 7, and the detector 8 in precise locations so that they align with the fill, not shown in FIG. 1, within the munition 2. The table 9 is machined with pockets 10 that receive the legs 11 to provide a constant height for the table 9. The detector 8 is aligned by a recessed region 20, which is machined into the table 9. The legs 11 are preferably adjustable so that an operator can match the centerline height of the detector 8 to the height of the fill center of mass of the munition 2. Furthermore, the adjustable legs 11 accommodate uneven ground surfaces in order to level the table 9.

For most munitions a few centimeters of misalignment among the components comprising the system 1, either horizontally or vertically, has no measurable effect on the PINS assay. This is because the neutrons emitted by the source 3 efficiently probe a large area, i.e., a 30 centimeter by 30 centimeter area, of the munition 2 in a representative embodiment. Only when the fill dimensions are as small or smaller than the detector crystal, not shown, within the detector 8, will misalignment by a few centimeters reduce the sensitivity. Therefore, for a relatively small munition 2, it is important that the fill center of mass be aligned with the centerline of the detector 8. For example, with regard to a relatively small munition 2, the fill center of mass may have to be aligned within about one centimeter of the centerline of the detector 8. In order to facilitate alignment, the munition 2 may be x-rayed prior to the PINS assay to accurately establish the location of the fill within the munition 2.

Figure 2:
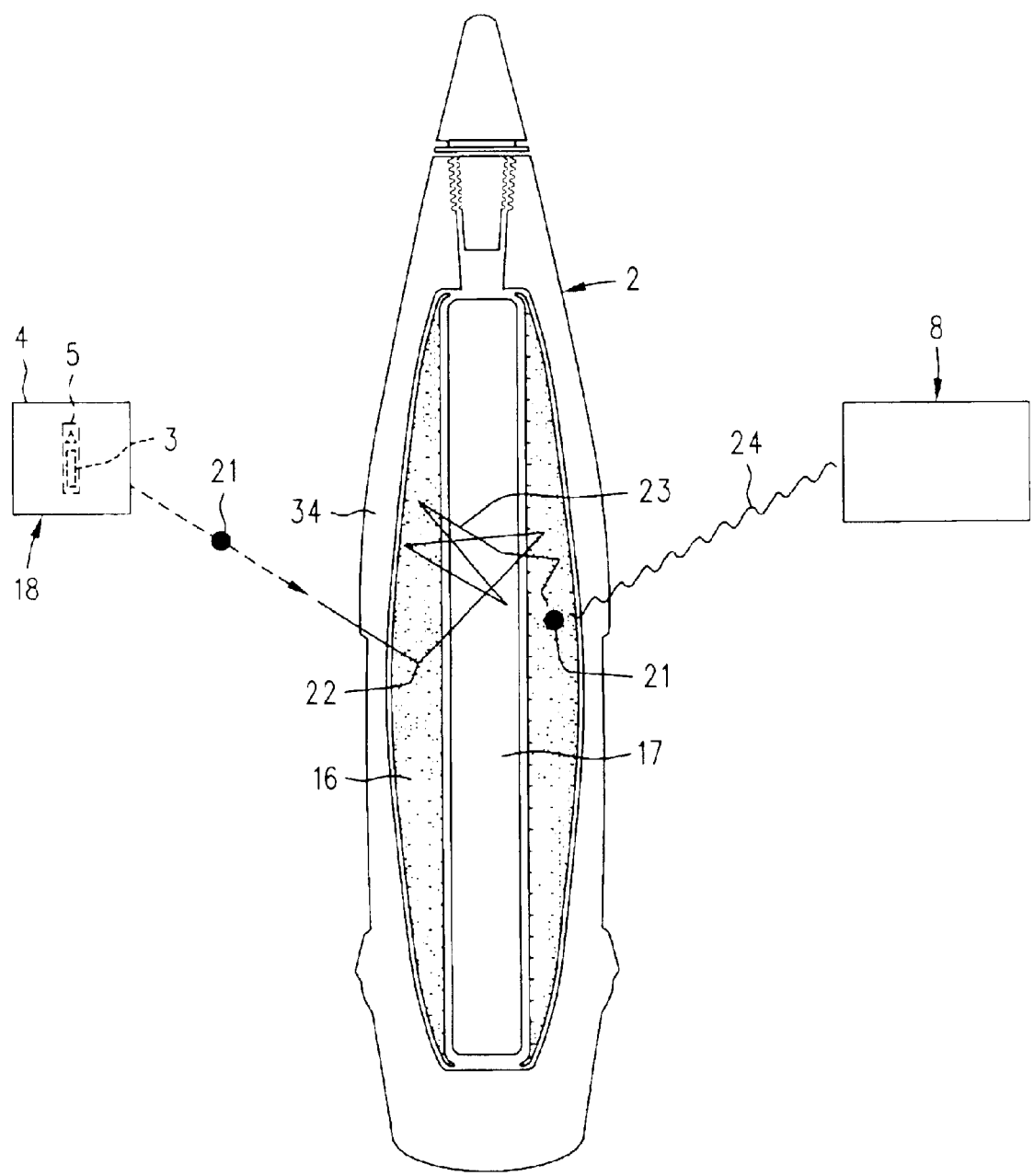
FIG. 2 is a cut away schematic illustration of the munition shell of FIG. 1 showing a neutron-induced reaction occurring in the fill agent within the artillery shell.

FIG. 2 is a schematic illustration, partly in cross-section, of the munition 2 undergoing prompt gamma-ray neutron activation analysis as described herein. The munition 2 contains a burster 17 and a chemical warfare fill agent 16 (sometimes referred to herein simply as the ("agent"). In summary, neutrons 21 emitted by the neutron-emitting assembly 18 pass through a steel casing 34 associated with the munition 2 to interact with the agent 16.

In a typical neutron-induced nuclear reaction within the munition 2, a neutron 21 has passed through the steel casing 34 of the munition 2. Upon interaction with the agent 16, the neutron 21 scattered. A point 22 illustrates the location where the neutron 21 began to scatter. The neutron 21 then slowed down and was captured by an atomic nucleus of the agent 16. A path 23 depicts a path that the neutron 21 followed. When an atomic nucleus of the agent 16 is excited by its interaction with a neutron 21, the atomic nucleus emits one or more characteristic gamma rays 24. The gamma ray 24 penetrated the casing 34 of the munition 2 and was counted by the detector 8. It should be noted that the gamma rays 24 passed through the collimator 7, which is not illustrated in FIG. 2. It should be noted that in practice, a plurality of neutrons 21 are emitted by the neutron-emitting source 18 and a plurality of gamma rays are emitted by nuclei of the agent 16.

Each chemical element emits a characteristic gamma-ray energy spectrum and intensity pattern in response to neutron bombardment. Hence, the chemical elements within the agent 16 inside the munition 2 can be identified by the neutron-induced gamma-ray spectral data associated with the agent 16. The chemicals comprising the agent 16 are inferred or otherwise assessed from the presence and relative abundance of various key chemical elements. When the chemical elements are identified and qualified, the agent 16 itself is readily identified.

As described above, the agent 16 is identified by its chemical elemental composition. For example, military explosives contain relatively large quantities of nitrogen. Thus, if the agent 16 contains relatively substantial amounts of nitrogen, it can be inferred that it is a high explosive. Several chemical warfare agents, such as mustard gas and lewisite, contain chlorine. All nerve agents contain phosphorous. Smoke munitions may contain phosphorous or chlorine, but in very different elemental ratios compared with chemical warfare agents. Unarmed practice munitions are commonly filled with sand or water/antifreeze mixtures.

Figure 3:
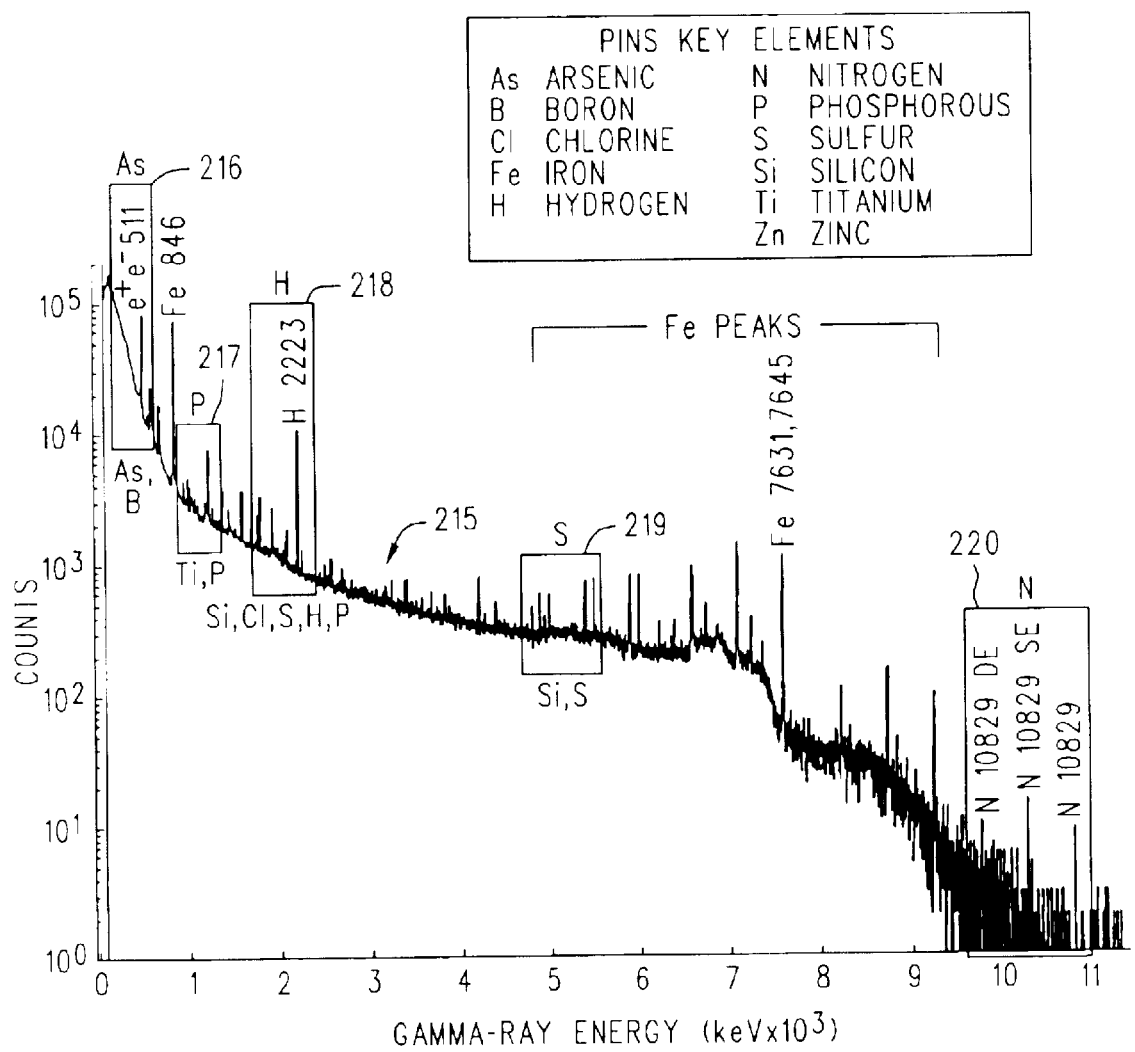
FIG. 3 is a neutron-induced gamma-ray spectrum indicating spectral regions of interest associated with several key chemical elements and their respective energy peaks.

Referring to FIG. 3, which is an example of a spectrum 215 of a high explosive munition, the PINS gamma-ray energy spectrum 215 illustrated therein extends from about 190 keV to about 11.2 MeV. The strongest gamma-ray peaks of the key elements for PINS munition assessments are in five energy intervals or regions of interest (ROIs). These energy ROIs are referenced as follows: the arsenic (As) ROI 216, the phosphorus (P) ROI 217, the hydrogen (H) ROI 218, the sulfur (S) ROI 219, and the nitrogen (N) ROI 220. As shown in FIG. 3, the arsenic ROI 216 extends from about 190 keV to about 550 keV. The phosphorus ROI 217 extends from about 1.0 MeV to about 1.5 MeV. The hydrogen ROI 218 extends from about 1.8 MeV to about 2.5 MeV. The sulfur ROI 219 extends from about 4.8 MeV to about 5.6 MeV. The nitrogen ROI 220 extends from about 9.6 MeV to about 11.2 MeV. Analysis of these energy regions determines the presence of several chemical elements including: arsenic, boron, chlorine, iron, hydrogen, nitrogen, phosphorous, sulfur, silicon, titanium, and zinc. The different chemical compounds that may comprise the agent 16, FIG. 2, have unique ratios of the above-described chemical elements. By analyzing the chemical elements constituting the agent 16, the ratios of the chemical elements are determined. Based on these ratios, the chemical compound or mixture within the agent 16 can be readily determined. In this manner, the agent 16 may then be qualitatively characterized.

Figure 4:
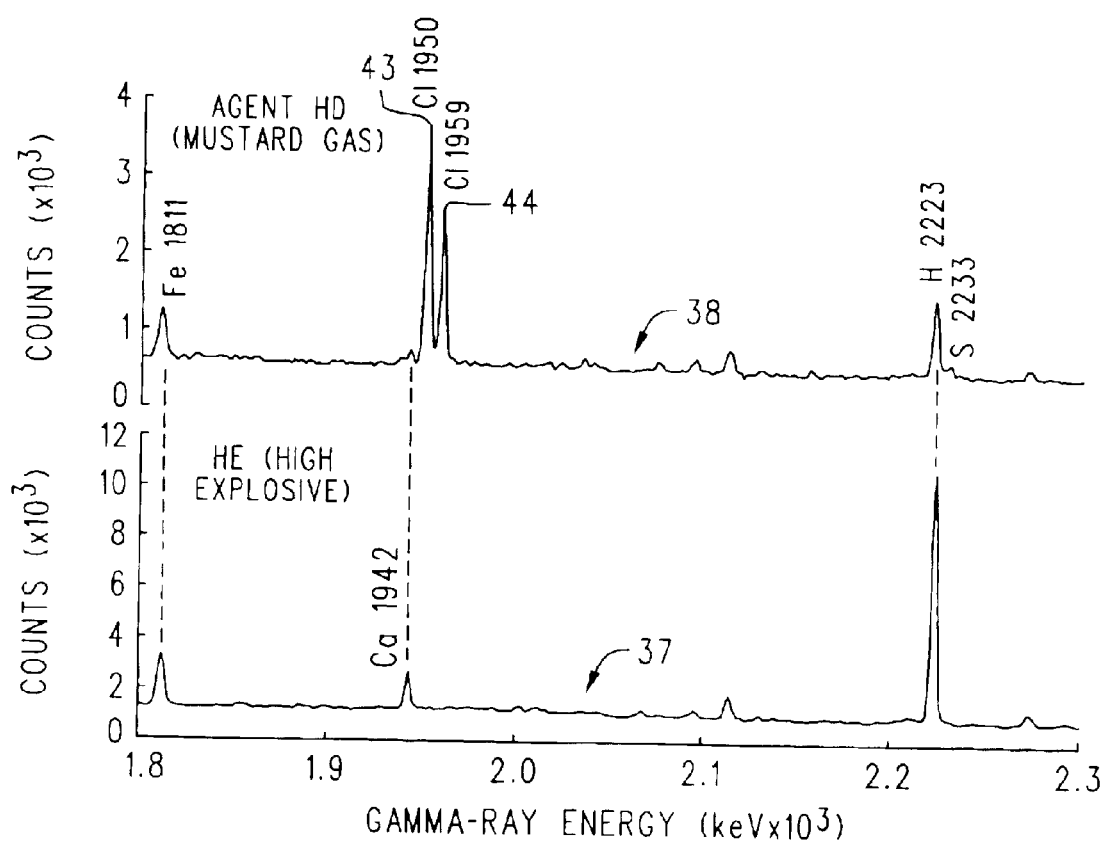
FIG. 4 illustrates gamma-ray spectra in the 1,800 to 2,300 keV region for the detection of mustard gas and high explosives in a chemical agent.
Figure 5:
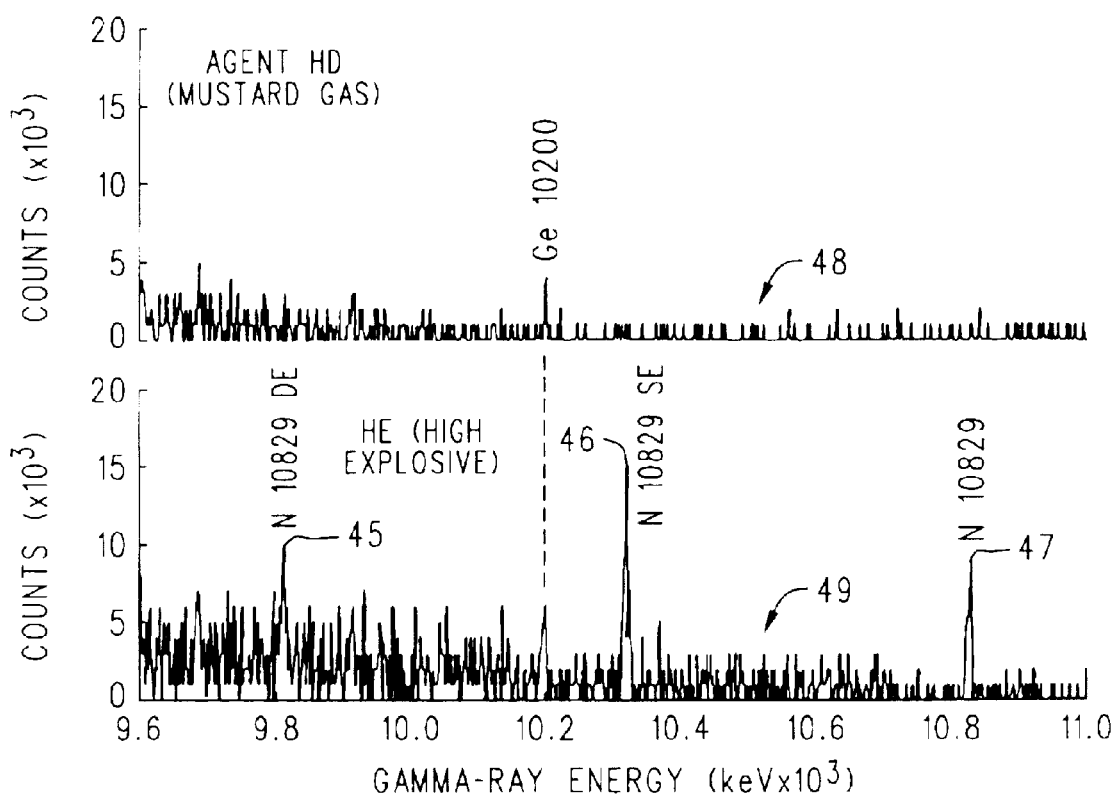
FIG. 5 illustrates gamma-ray spectra in the 9,600 to 11,000 keV region showing the presence of nitrogen peaks in high explosives and the lack of nitrogen peaks in mustard gas.

To illustrate the differences between ratios of chemical elements comprising different agents, examples of the differences between mustard gas and high explosives PINS spectra are shown in FIGS. 4 and 5. Referring to FIG. 4, the PINS spectrum 38 of mustard gas, also known as HD, is compared with the spectrum 37 for a high explosive, also known as HE, in the hydrogen ROI of 1,800 to 2,300 keV. This region corresponds to the hydrogen ROI 218 of FIG. 3. As shown in FIG. 4, chlorine peaks 43 and 44 of 1,950 keV and 1,959 keV, respectively, are evident in the mustard gas spectrum 38, but absent from high explosive spectrum 37. Accordingly, the spectrums 37 and 38, in summary, show that chlorine is prevalent in mustard gas and nonexistent in high explosives. The spectra 37 and 38 also show peaks corresponding to iron at 1,811 keV and calcium at 1,942 keV. The iron is attributed to the casing 34, FIG. 2, of the munition 2 which, in this example, is made of steel. The calcium present in both spectra 37 and 38 is attributed to cement walls of the ammunition bunker in which the munition 2, FIG. 2, was analyzed.

Additional differences between mustard gas and high explosives are illustrated in FIG. 5, which shows a spectrum 48 of mustard gas and a spectrum 49 of high explosives in the nitrogen 9,600 keV to 11,000 keV region. This region has been referenced in FIG. 3 as the nitrogen ROI 220. As shown in FIG. 5, nitrogen peaks, designated at numerals 45, 46, and 47, of the gamma ray spectrum 49 are dominant for the high explosive agent, but not present in spectrum 48 of the mustard gas agent.

Referring again to FIGS. 1 and 2, having described the components comprising the system 1, the operation of the system 1 will now be summarized. The following non-limiting description describes the use of system 1 to determine the chemical elements within the agent 16. Based on the chemical elements associated with the agent 16, the system 1 identifies the agent 16. The agent 16 described herein is located within the munition 2. It is to be understood, however, that the operation of the system 1 is not to be limited entirely to identifying agents located within munitions. The system 1 may also be used to identify other agents whether or not they are located within containers, such as munitions.

Figure 6:
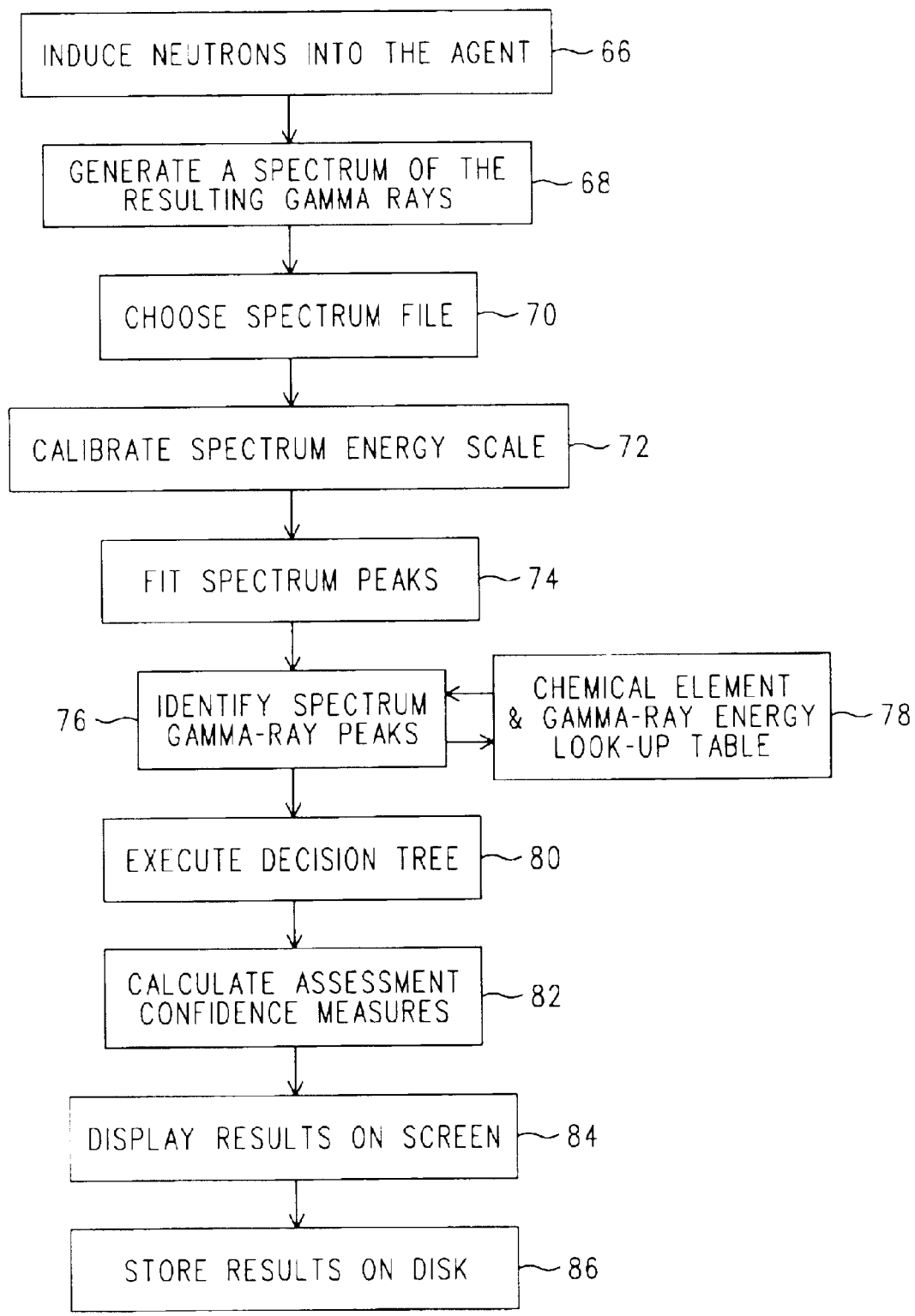
FIG. 6 is a flow chart that summarizes the operation and calibration of the system of FIG. 1.

A non-limiting embodiment of a method of operation for the system 1 is summarized by the flow chart of FIG. 6. The non-limiting method illustrated in FIG. 6, with referenced to FIGS. 1 and 2, commences with a step 66 of inducing neutrons 21 into the agent 16. A step 68 then generates a spectrum of the gamma-ray energy levels that result from the neutrons 21 being induced into the agent 16.

In step 70, analysis of the spectrum begins with the system operator choosing a spectrum file for calibration. In addition to spectral information on the fill chemicals, the spectrum file also includes "background" gamma-ray peaks of known energies. These background peaks can be used to establish the energy calibration of the spectrum generated by the fill 16, FIG. 2. For example, the spectrum recorded from steel containers produces an extensive set of iron gamma-ray peaks. When the spectrum file has been chosen, a step 72 involving calibration of the spectrum energy scale is performed. The gamma-ray energies of the peaks in the spectrum are fit versus the peak centroid channels via a conventional least-squares algorithm. A step 74 performs a directed fit of the key element gamma-ray peaks. Steps 76 and 78 identify peaks in the spectrum and determine the chemical elements corresponding to the peaks. When the chemical elements have been determined, a step 80 is performed, which executes a decision tree. The decision tree identifies the agent 16 based on the chemical elements within the agent 16. The method then performs a step 82, which calculates the confidence of the identification of the agent 16. The identity of the agent 16 and the confidence of the identification is displayed per step 84 and stored per step 86.

Having summarily described a non-limiting embodiment of identifying an agent, a more detailed description of the identification process will now be presented. Referring to FIGS. 1 and 2, the following description of the identification process is based on identifying the agent 16 located within the munition 2. It shall again be understood, however, that the method described herein may be applicable to identifying other agents whether or not they are located in containers.

Identifying the agent 16 commences with calibrating the gain of the system 1, which is normally accomplished when the system is powered up. The electronic gain of the high purity germanium (HPGe) detector within the detector 8 may, as a non-limiting example, be adjusted to place the 2.2 MeV hydrogen capture gamma-ray peak at 20 percent of full scale and in channel 1,600 of the multichannel analyzer 27. Therefore, full scale of an acquired spectrum will be five times the energy of the hydrogen peak or about 11 MeV. This setting insures that the highest energy gamma ray of interest, which is the 10.8 MeV nitrogen capture gamma ray, will be on scale.

Obtaining the gamma-ray emission of hydrogen may be accomplished by having the detector 8 count emissions from the moderator block 4. The neutrons 21 emitted by the source 3 within the moderator block 4 react with the hydrogen atoms in the polyethylene of the moderator block 4 and generate gamma-ray emissions. These gamma-ray emissions from the hydrogen are typically very abundant and are readily counted by the detector 8. An operator of the system 1 establishes the correct amplifier gain by repeated adjustments until the hydrogen capture gamma-ray peak appears within ten channels of channel 1600 for the multichannel analyzer 27 described herein.

When the gain has been set, the system 1 may be used to identify the agent 16. The method of identifying the agent 16 within the munition 2 commences with arranging the system 1 as shown in FIG. 1 and described above. More specifically, the neutron-emitting assembly 18 is placed adjacent the munition 2. The collimator 7, open at both ends, surrounds the detector 8.

The source 3 emits neutrons 21 that pass through the casing 34 of the munition 2 where they react with the agent 16 as outlined above. The location of the source 3 within the polyethylene moderator block 4 causes some of the neutrons 21 to pass from the source 3 directly to the munition 2. These neutrons 21 are also known as "fast neutrons." Other neutrons interact with the polyethylene in the moderator block 4. These neutrons are known as "slow neutrons." Accordingly, the placement of the source 3 close to the surface 19 of the moderator block 4 creates a variety of fast and slow neutrons, which improves the PINS assessment sensitivity.

The neutrons 21 scatter upon contact with the agent 16. The path 23 illustrates an example of the path taken by a scattering neutron 21. When a neutron 21 collides with a nucleus of a chemical element within the agent 16, the nucleus emits a gamma ray 24. The gamma ray 24 has an energy that is characteristic of the chemical element that produced it. The gamma ray 24 passes through the casing 34, through the collimator 7, and into the detector 8.

It should be noted that some of the neutrons 21 will collide with nuclei of chemical elements in the casing 34. The casing 34 may be comprised of steel and, thus, may contain iron. As will be described below, iron may be used as a reference for further calibration purposes. Accordingly, if the casing is of a type that does not contain iron, an object, such as a steel object, may be placed in the proximity of the casing 34 to react with the neutrons 21. The iron in the object will generate gamma rays having energies characteristic of iron, which may be used for calibration.

As described above, the collimator 7 serves to keep background or extraneous gamma rays from being detected by the detector 8. Generally, only gamma rays that are generated by the agent 16 or the casing 34 will be able to pass through the collimator 7 and into the detector 8. Accordingly, the collimator 7 reduces the probability that the detector 8 will detect gamma rays generated by other objects. In general, however, the detector 8 does detect at least some gamma rays generated by other sources.

The detector 8 generates electrical pulses proportional in voltage to the energies of the gamma rays it detects. Accordingly, the output of the detector 8 will reflect gamma rays having various energies. These various energies correspond to gamma-ray emissions from the casing 34 and the agent 16, as well as other sources. For example, some neutrons 21 may interact with the table 9 or a wall surrounding the system 1. These interactions will generate gamma rays that may be detected by the detector 8. These gamma rays may, as examples, be characteristic of aluminum comprising the table 9 or cement comprising the walls, and will reflect the chemical elements associated with aluminum and cement.

The detector 8 outputs the voltage pulses to the multichannel analyzer 27. The multichannel analyzer 27 digitizes and sorts the energy data into discrete channels, wherein each channel corresponds to a small energy interval. The multichannel analyzer 27 also keeps track of the number of gamma rays that are detected within each energy interval or channel by forming a histogram of "pulses" or "hits" per channel wherein each hit or pulse is representative of a gamma-ray detection. The histogram is a digitized gamma-ray energy spectrum, and a copy is passed to the computer 28 for display and analysis.

Analysis of the spectrum commences with calibrating the energy scale of the histogram (referred to herein simply as the "spectrum") generated by the multichannel analyzer 27. Calibration, in summary, is the process of relating the spectrum channels to known gamma-ray energies. These energies are the results of gamma-ray emissions from chemical elements of known, standardized compounds. In a non-limiting calibration example described below, the chemical elements are primarily iron and chlorine. Iron is typically abundant in casings 34 made of steel and chlorine is abundant in some munitions. If neither iron nor chlorine is detected, the operator of the system 1 may place a steel object in the vicinity of the munition 2 so that the steel object emits gamma rays characteristic of iron. These gamma rays are then detected along with the gamma rays from the fill chemical and used for calibration purposes.

Figure 7A:
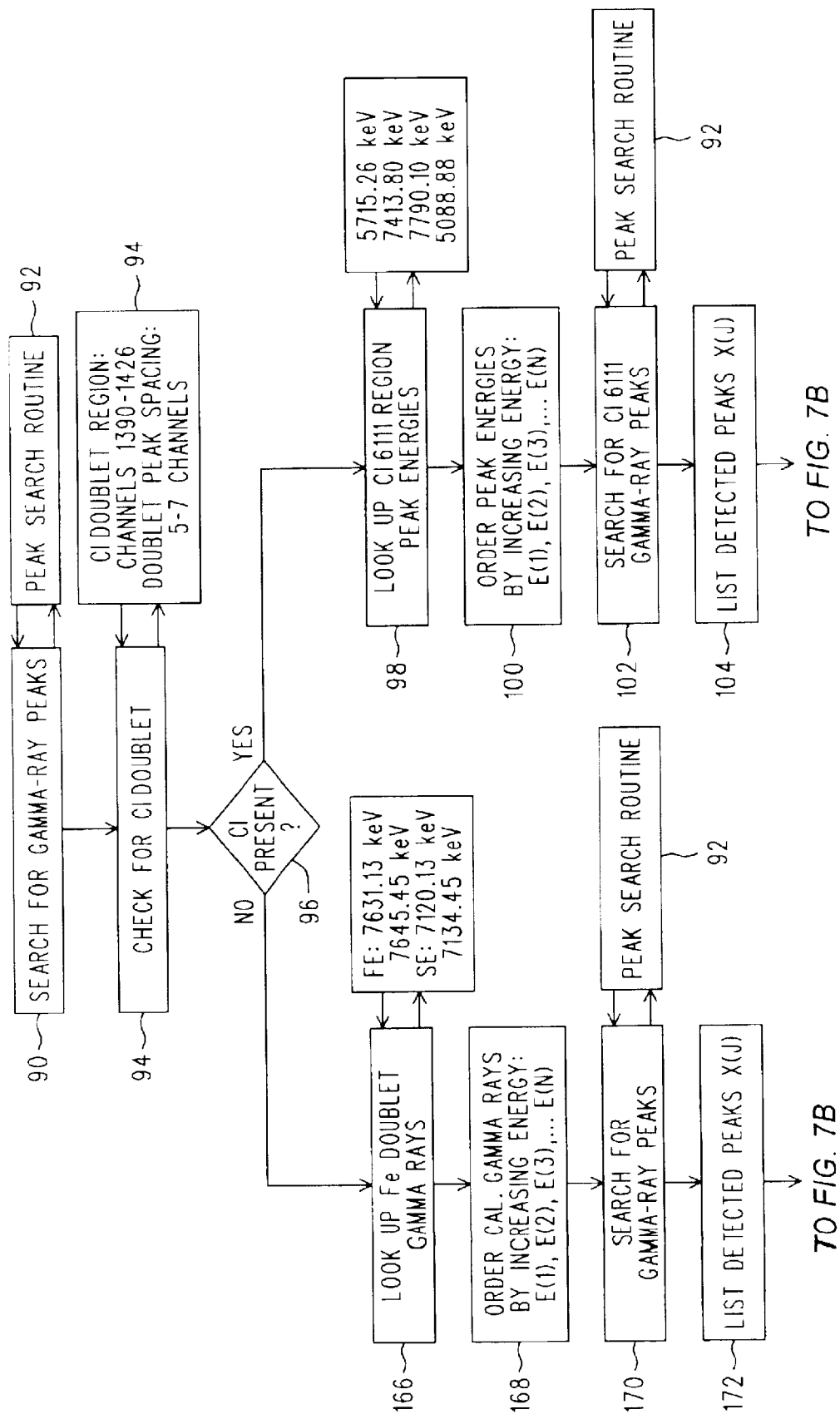
FIGS. 7A and 7B collectively constitute a flowchart that illustrates a calibration method for the system of FIG. 1.
Figure 7B:
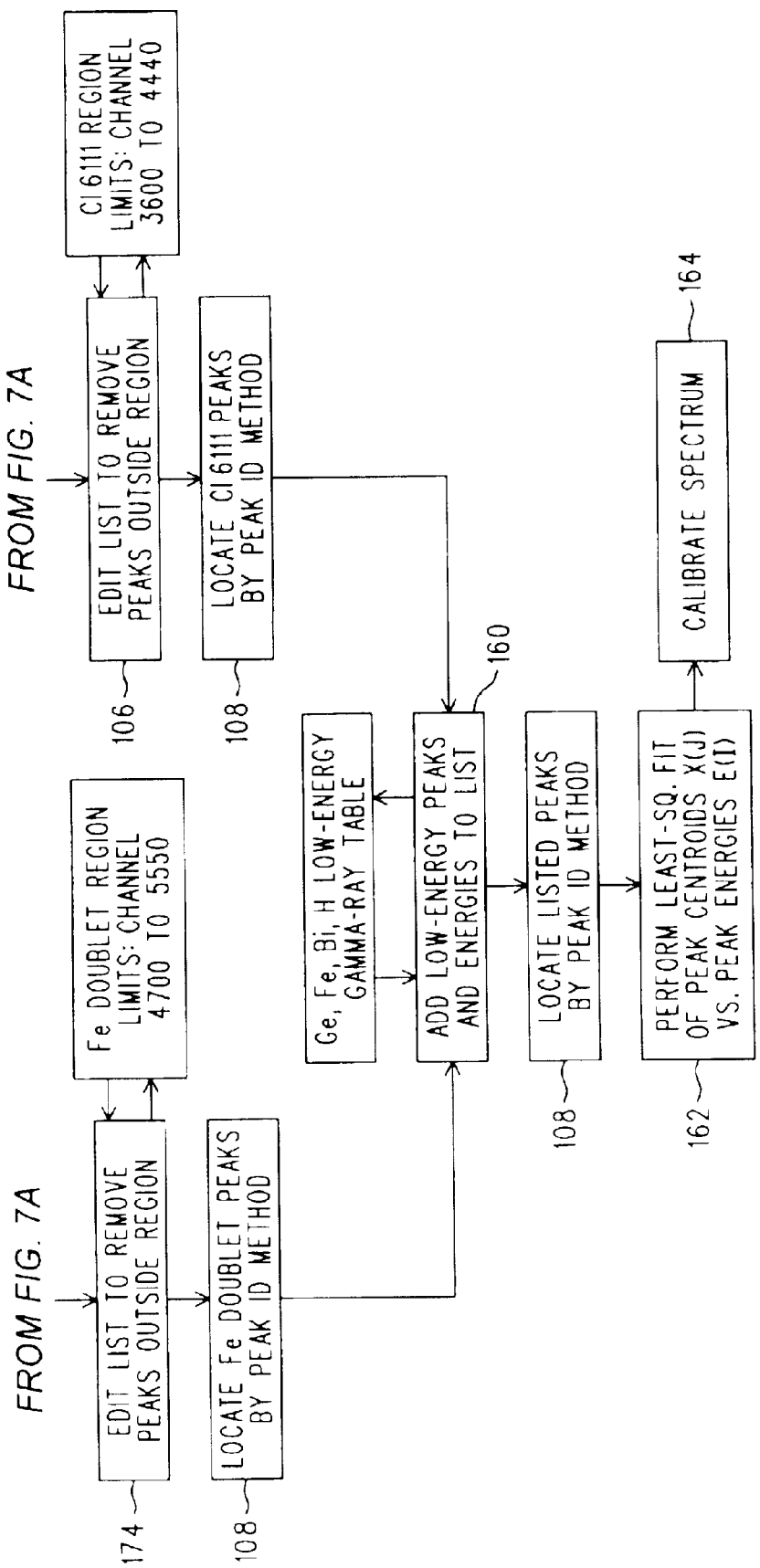

The energy calibration method is described in detail by the flow chart of FIGS. 7A and 7B. Energy calibration commences with the step 90 of searching the spectrum for peaks. A conventional peak searching routine step 92 may be used to accomplish the search. The peaks are analyzed per a step 94 to determine if a chlorine doublet is present in the spectrum. The chlorine doublet would be within the channels 1,390 to 1,426 and the peak spacing of the doublet would be between five and seven channels. A decision 96 is then made as to whether the chlorine doublet is present in the spectrum.

The following description assumes that chlorine is present in the spectrum and calibrates the spectrum based on chlorine. If, in the alternative, chlorine is not present, the spectrum is calibrated based on iron. A description of calibrating the spectrum based on iron follows the calibration based on chlorine.

The first step 98 in the chlorine calibration process involves looking up the energy peaks emitted by chlorine. The computer 28, FIG. 1, may have a table (sometimes referred to as a "look up table") with the calibration gamma-ray peak energies stored therein. The gamma-ray energies used in the following calibration example are 5,088.88 keV, 5,715.26 keV, 7,413.80 keV, and 7,790.16 keV. It should be understood that more than four energies may be used in the calibration procedure. The number of energies used is equal to the variable "N" for future reference. In the next step 100, the energies are arranged in increasing order, noted as E(1), E(2), E(3), and E(4). In the situation where more energy peaks are used, the energy levels are arranged from E(l) to E(N), wherein E(N) is the maximum energy. The energies may, as an alternative, be arranged in decreasing order. A search at step 102 is conducted of the spectrum to locate the chlorine gamma-ray peaks in the spectrum. The peak search routine 92 is used for this task. At step 104, the gamma-ray peaks of chlorine found in the spectrum are listed and stored as X(l) to X(J), which is described with reference to FIGS. 8A and 8B. At this point, step 106 removes the peaks that lie outside the chlorine region. The chlorine region used in this example is between channels 3,600 and 4,440.

At this point, the computer 28 has looked up gamma-ray energies corresponding to chlorine and has found peaks that may correspond to chlorine from the spectrum. Step 108 determines which energy peaks in the spectrum actually correspond to chlorine by the use of a "peak identification method." The peak identification method is illustrated by the flow chart of FIGS. 8A and 8B. The peak identification method will now be described in detail, followed by a resumption of the calibration method illustrated in FIG. 7B at step 108. The peak identification method is used in different locations during calibration for use with chlorine, iron, and other elements. In the following description, the peak identification method is discussed with reference to chlorine. It shall be understood, however, that the following description may be applied to identifying chemical elements other than chlorine.

Figure 8A:
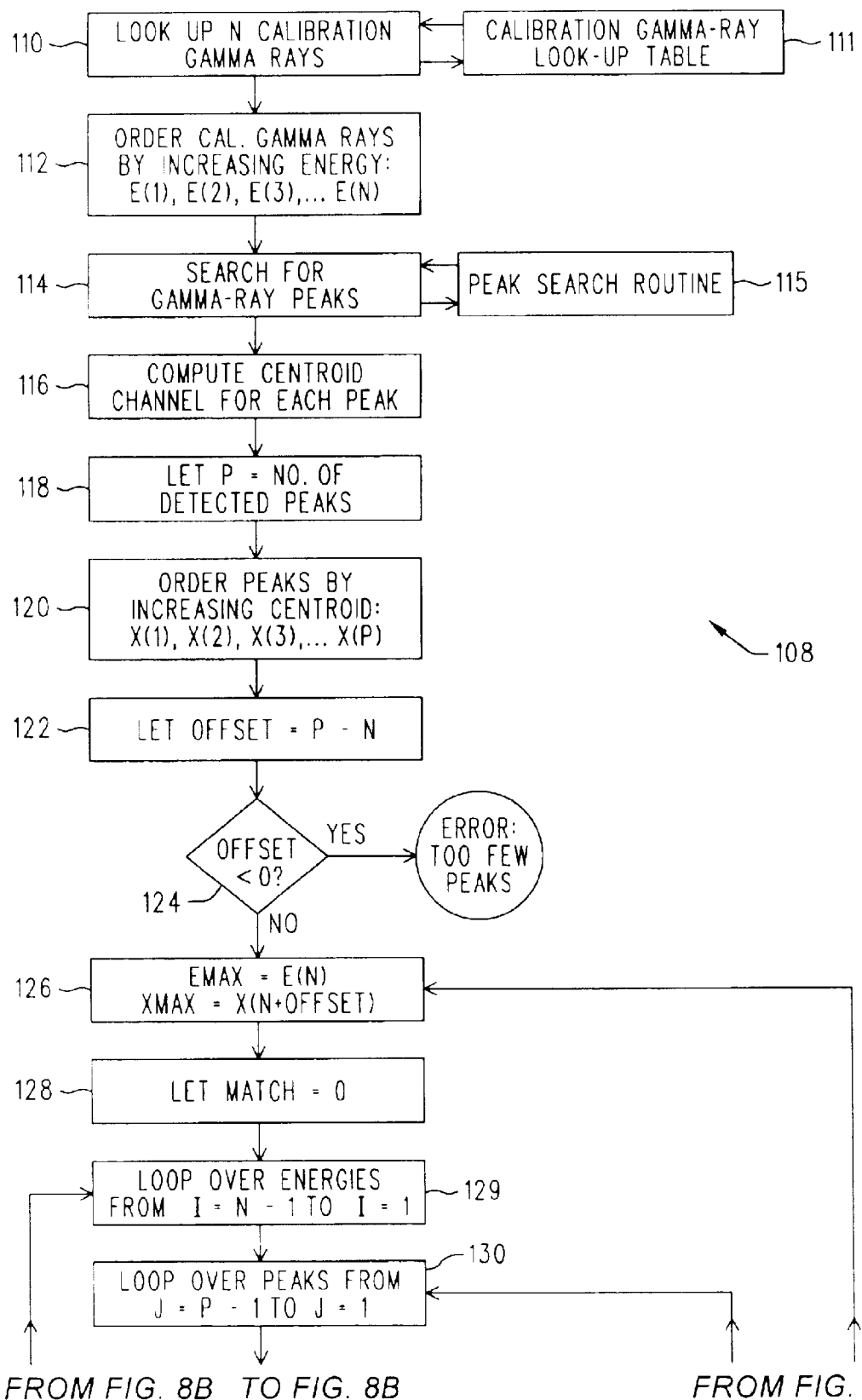
FIGS. 8A and 8B collectively constitute a flowchart that illustrates a peak identification method used by the flow chart of FIGS. 7A and 7B.
Figure 8B:
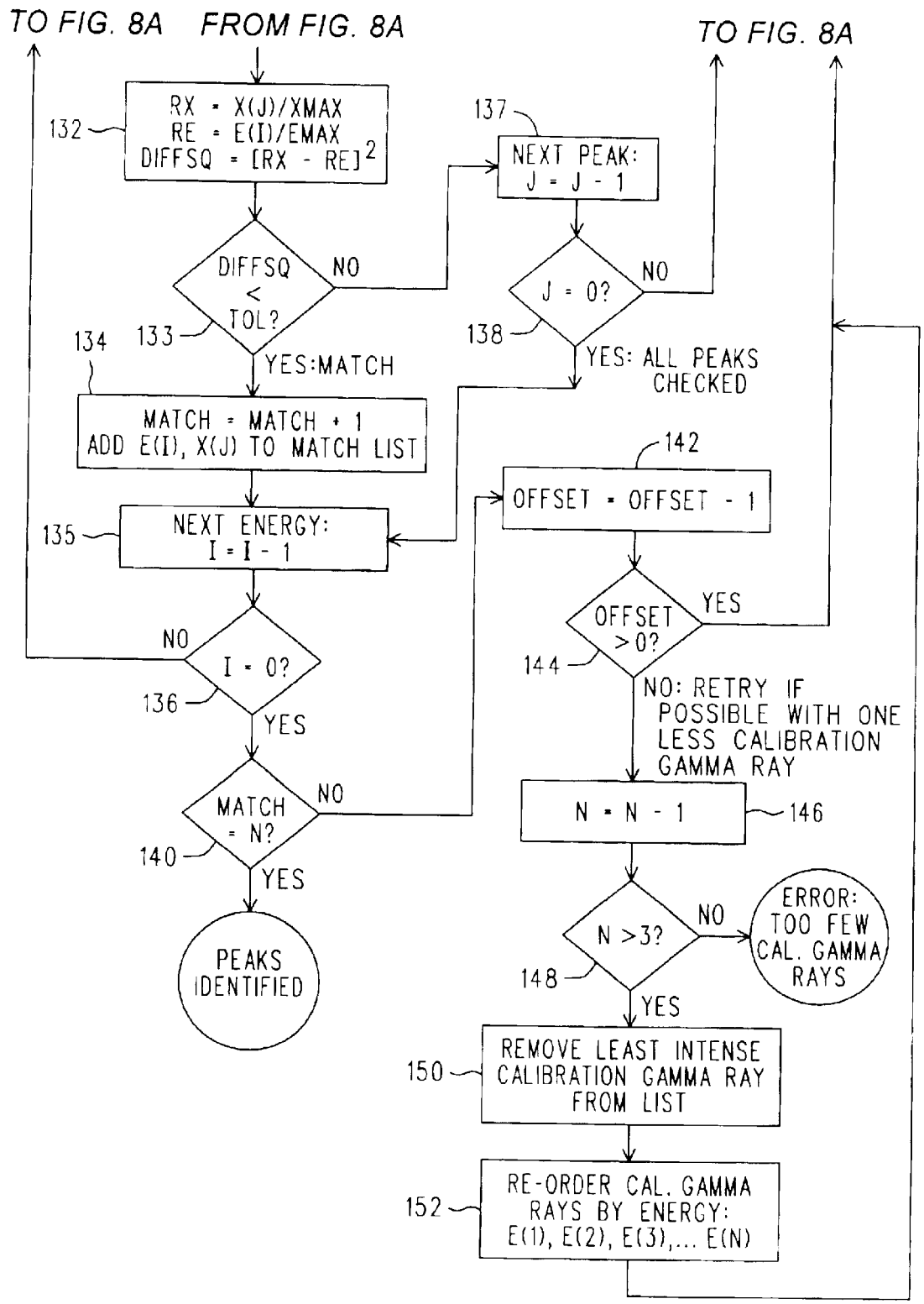

The flow chart of FIGS. 8A and 8B describes the peak identification method. It should be noted that the steps 110 through 115 of the flow chart of FIG. 8A basically correspond to the steps 98, 100, and 102 of the flow chart of FIG. 7A and have already been accomplished. Step 116 of the peak identification method computes the channel where the centroids of the energy peaks in the spectrum were measured. Step 118 assigns a variable "P" as the number of peaks that were detected in the spectrum. Step 120 places the peaks in increasing order and assigns the values of the peaks to the variables X(1), X(2), X(3) to X(P). Step 122 creates a variable referred to as "OFFSET" which is equal to the number of detected peaks, P, of the spectrum minus the number of peaks, N, of a look up table. A decision 124 is made to determine if the OFFSET is less than zero. If the OFFSET is less than zero, then there are more peak energies in the calibration table than were found in the spectrum and testing cannot proceed. An indication of this problem may be sent to the operator and more data may be collected to repeat the test. If the OFFSET is equal to or greater than zero, then enough peaks were found in the spectrum to continue with the peak identification method.

The peak identification method proceeds to step 126 by assigning a variable EMAX equal to E(N). In addition, a variable XMAX is set equal to X(P). Accordingly, EMAX is equal to the value of the highest energy in the look up table. The variable XMAX is equal to the value of the highest peak centroid channel in the portion of the spectrum being analyzed. Step 128 creates a variable, MATCH, and sets it equal to zero. Steps 129 and 130 start loops, which will compare the values of the energy peaks in the look up table to the values of the energy peaks identified in the spectrum. Step 129 loops from I=N−1 to I=1. Step 130 is a nested loop from J=P−1 to J=1.

The correlations between the peaks in the spectrum and the energies in the look up table are measured at step 132. A ratio RX is calculated as the peak value of X(J) divided by the value of XMAX. Another ratio, RE, is calculated as the value of E(I) divided by the value of EMAX. A variable, DIFFSQ, is calculated as the square of the difference between RX and RE. If the peak in the spectrum corresponds to its respective energy in the look up table, then the ratio RX will be approximately equal to the ratio RE and the value of DIFFSQ will be minimal.

A decision 133 is then made to determine if DIFFSQ is less than a specific tolerance, TOL. The tolerance may, as an example, be 1%. The tolerance may, however, be set for specific measurement circumstances. If DIFFSQ is less than the tolerance, TOL, the peak in the spectrum corresponds to the peak in the look up table. Step 134 then increments the variable MATCH and adds E(I) and X(J) to a match list. The variable, MATCH, tracks the matches between energy peaks in the spectrum to energy peaks in the look up table. Step 135 decrements the variable I by one to compare the next energy peak in the look up table to the next energy peak in the spectrum. A decision 136 determines if the variable, I, is equal to zero. If I is not equal to zero, the loop continues at the step 129. If I is equal to zero, the loop ends and the process continues to step 140 as described below. Referring again to step 133, if DIFFSQ is greater than TOL, the energy peak in the spectrum did not match the energy peak in the look up table. Step 137 then decrements the variable J by one. A decision 138 is thereafter made to determine if J is equal to zero. If J is not equal to zero, the nested loop proceeds to step 130 to compare the next peak in the spectrum to the energy in the look up table. If, on the other hand, J is equal to zero, the process continues to the step 135 as described above.

If the variable, I, is equal to zero, a decision 140 is made to determine if the variable MATCH is equal to the variable N. In other words, a decision is made to determine if all of the ratios of the peaks in the spectrum correspond to the ratios of the energies in the look up table. If the variable MATCH is equal to N, the peak identification method has been successful completed. If, on the other hand, the energy peaks were not correctly matched, the method makes appropriate provisions to attempt to locate other energy peaks in the spectrum.

The first step in locating other energy peaks is step 142, which reduces the OFFSET variable by one. A decision 144 assures that the OFFSET variable remains greater than zero. If so, the method moves to step 126 with the new OFFSET value. The decremented OFFSET value will attempt to cause the above-described loops to match a second group of peaks in the spectrum to the energies in the look up table. The second group of peaks uses the second-highest peak as XMAX. This process of decrementing the OFFSET will continue until either a match is found or the OFFSET becomes less than zero. If the OFFSET becomes equal to zero, the variable N is decremented at step 146. A decision 148 determines if the variable N is greater than three. If the variable N is not greater than three, then there are not enough peaks in the spectrum to proceed. The peak identification attempt is terminated. If, on the other hand, the variable N is greater than three, step 150 removes the least intense peak from the lists. The energy peaks are then reordered at step 152 and another attempt is made to create a match by proceeding to step 126.

Referring again to the flow chart of FIGS. 7A and 7B, upon completion of the peak identification method of step 108, the calibration method proceeds to step 160.

Step 160 adds lower energy gamma-ray peaks to the list of energies. The lower energy peaks illustrated in FIGS. 7A and 7B are gamma-ray emissions corresponding to germanium, iron, bismuth, and hydrogen. It should be noted that other elements may be utilized for lower energy peaks. These lower energy peaks are located by the peak identification method of step 108 as described above with reference to the flow chart of FIGS. 8A and 8B. When all the energy peaks have been determined, step 162 performs a least square fit of the peak centroids X(J) versus the peak energies E(I). The spectrum is then calibrated per step 164.

A least-squares fit of peak energy vs. peak centroid determines the linear or quadratic relationship between gamma-ray energy and spectrum channel number. The input to the least-squares routine is the list of gamma-ray peak centroids and energies determined by the peak ID method above. It should be noted that it is conventional in gamma-ray spectroscopy to determine the x-intercept and the slope of the line mapping energy to channels. The quadratic term, if any, is usually a very small correction, the order of $10^{-6}$ or less. The x-intercept is termed the "DC offset," and can be adjusted on the multichannel analyzer 27, FIG. 1, to be a few channels or less. The slope is referred to as the "conversion gain," and is expressed in keV per channel.

Referring again to step 96, the above-described calibration method was based on calibration using chlorine. If, however, chlorine is not present in the spectrum, the calibration may be performed based on iron. The steps 166, 168, 170, 172, and 174 for calibrating the spectrum using iron are virtually identical to the above-described steps 98, 100, 102, 104, and 106 for calibrating the spectrum using chlorine. The step 166, however, looks up energy peaks of 7120.13 keV, 7134.45 keV, and 7631.13 keV, 7645.45 keV, which correspond to peak energies of iron. It should be noted that elements other than chlorine and iron may be used to calibrate the spectrum.

Having described the peak identification method and the calibration method, examples of their use will now be described. The following two examples are based on energy peaks, E(I), from a look up table (Table I) as follows:

TABLE I

| Energy (keV) | Intensity (gamma rays/100 disintegrations) |
|---|---|
| 2,000 | 90 |
| 5,000 | 75 |
| 7,000 | 20 |
| 10,000 | 85 |

In the first example, four gamma-ray peaks are detected with centroids in channels 1429, 3571, 5000, and 7143. The method (or computer program) makes the starting assumption that the highest energy peak corresponds to the highest energy gamma ray, which is correct in this example. Thus, the method sets EMAX equal to 10,000 keV and XMAX equal to 7143. The method then computes the ratio of each lower energy peak's centroid value to the value of XMAX. The method then compares this ratio to the ratios of the calibration gamma-ray energies. For the next-highest calibration energy and gamma ray peak, these ratios are 7000/10000, which is equal to 0.7 and 5000/7143, which is also equal to 0.7. The ratios are than compared to each other to determine if they are equal within a specified tolerance, i.e., one or two percent. If the ratios are within the tolerance, the gamma-ray energy peak and calibration energy peak are said to match. In this example, the peaks match.

The method loops over the calibration energy peaks in decreasing order. The next energy ratio is 5000/10000, which is equal to 0.5, and the next peak ratio is 3571/7143, which is equal to 0.499. The last calibration energy ratio is 2000/10000, which is equal to 0.2, and the corresponding peak ratio is 1429/7143, which is equal to 0.2001. If all the ratios are within the tolerance, the peaks match, as they do in this example, and the peak identification method is complete.

Upon completion of the peak identification method, a least-squares fit of energy peaks versus centroid peaks determines the linear or quadratic relationship between gamma-ray energy levels and spectrum channel number. The input to the least-squares fit routine is the list of gamma-ray centroid peaks and energy levels determined by the peak identification method discussed above. It should be noted that it is conventional in gamma-ray spectroscopy to determine the x-intercept and the slope of the line mapping energy to channels. The quadratic term, if any, is usually a very small correction, i.e., an order of $10^{-6}$ or less. The x-intercept is termed a DC offset and can be adjusted on the multichannel analyzer 27 to be a few channels or less. The slope is known as the conversion gain and is expressed in keV per channel. In this example, the DC offset is 0 channels, and the conversion gain is 1.4 keV/channel.

In the second example, three gamma-ray peaks are detected with centroids in channels 1429, 3571, and 7143. It should be noted that the lowest-intensity gamma-ray peak at channel 5000 is missing in this case.

The method again assumes that the peak in channel 7143 matches the 10,000 keV gamma ray. As the method steps through the successively lower-energy gamma rays, it attempts to match the 7,000 keV gamma ray to the next lower peak in channel 3571. The energy ratio is equal to 0.7 and does not equal the peak ratio 3571/7143, which is equal to 0.499. The method then loops to the lowest peak in channel 1429 and again fails to form a match because the peak ratio is 1429/7143, which is equal to 0.2001. The method then drops the lowest intensity gamma ray at 7,000 keV from the list and tries again. In this example it will successfully match the three peaks.

If, on the other hand, the match failed again, the program would drop the next-lowest intensity gamma ray from the list and try again, provided three or more gamma rays remain on the list. If only two gamma ray peaks remain, the peak identification program fails. Usually, this failure simply requires the user to count for a longer time interval, so that the weaker-intensity calibration gamma-ray peaks can be identified.

Having calibrated the spectrum, the system 1, FIG. 1, proceeds with identifying the agent 16, FIG. 2, located within the munition 2. The following is a non-limiting list of agents 16 and their corresponding abbreviations that are commonly contained within munitions and identified by the system 1:

CG Phosgene

CK Cyanogen Chloride

CW Chemical Warfare Agent

FM Smoke

FS Smoke

GB Nerve Agent (Sarin)

H Sulfur Mustard Gas

HC Smoke

HE High Explosive

HN Nitrogen Mustard Gas

L Lewisite

VX Persistent Nerve Agent

WP White Phosphorus Smoke

Sand

Water and Antifreeze

The above-listed agents are comprised of the following chemical elements, which will be identified by the system 1:

| | |
|---|---|
| As | Arsenic |
| B | Boron |
| Cl | Chlorine |
| H | Hydrogen |
| N | Nitrogen |
| O | Oxygen |
| P | Phosphorus |
| S | Sulfur |
| Si | Silicon |
| Ti | Titanium |
| Zn | Zinc |

Accordingly, with regard to the non-limiting examples of the operation of the system 1 described herein, the above-listed chemical elements will be identified in the agent 16. It is to be understood, however, that the system 1 may be modified and adapted to identify other agents and other chemical elements.

Having calibrated the spectrum, the computer 28 now analyzes the calibrated spectrum to identify the above-listed chemical elements within the agent 16. A conventional analysis program may serve to locate peaks in the spectrum and to identify the elements corresponding to the peaks. Because the spectrum is calibrated, the identification of the chemical elements is very accurate. The analysis may also serve to determine the ratios of the elements in the spectrum.

Figure 9A:
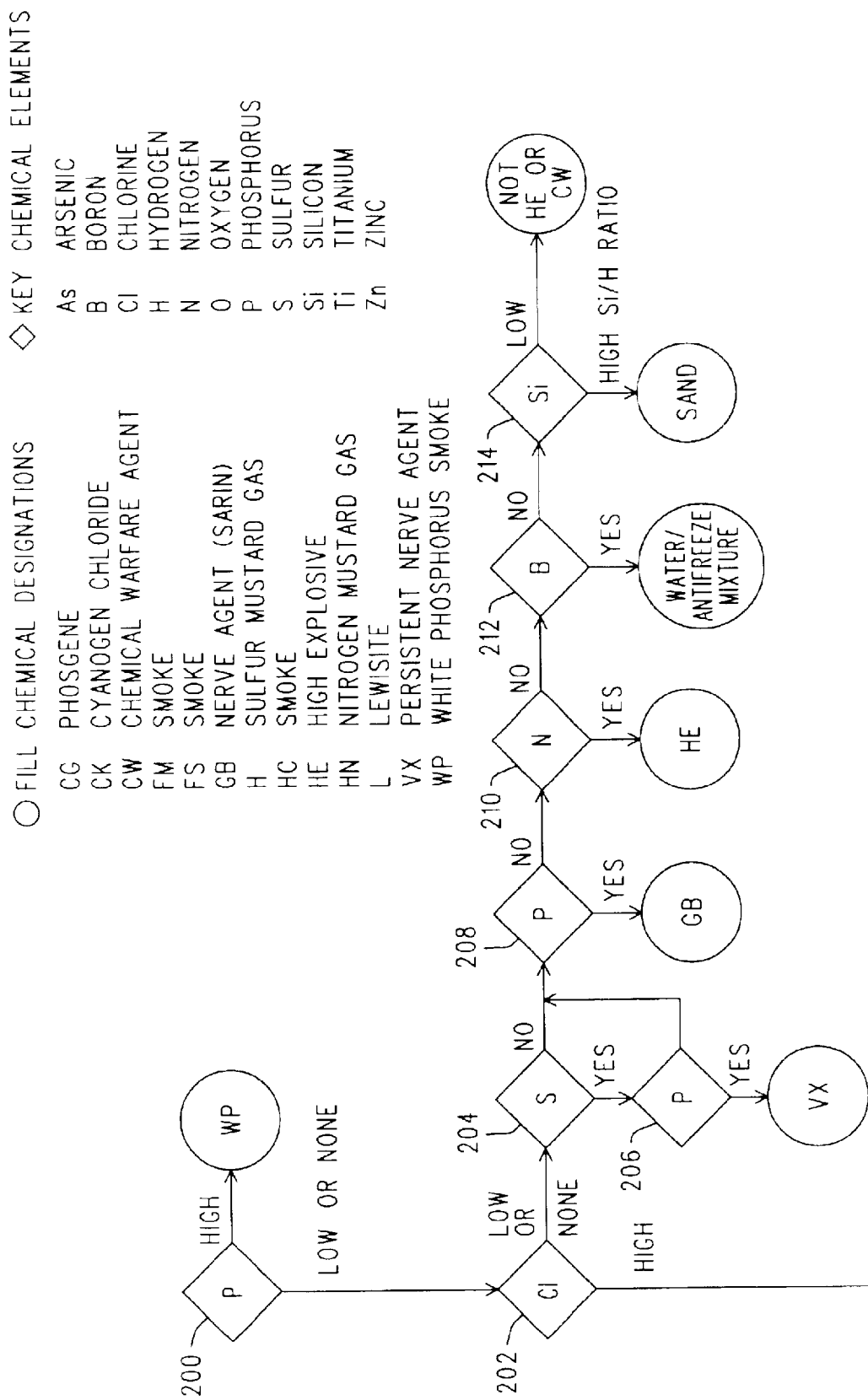
FIGS. 9A and 9B collectively constitute a flowchart of a decision tree algorithm that identifies the chemical agent within the munition of FIG. 2.
Figure 9B:
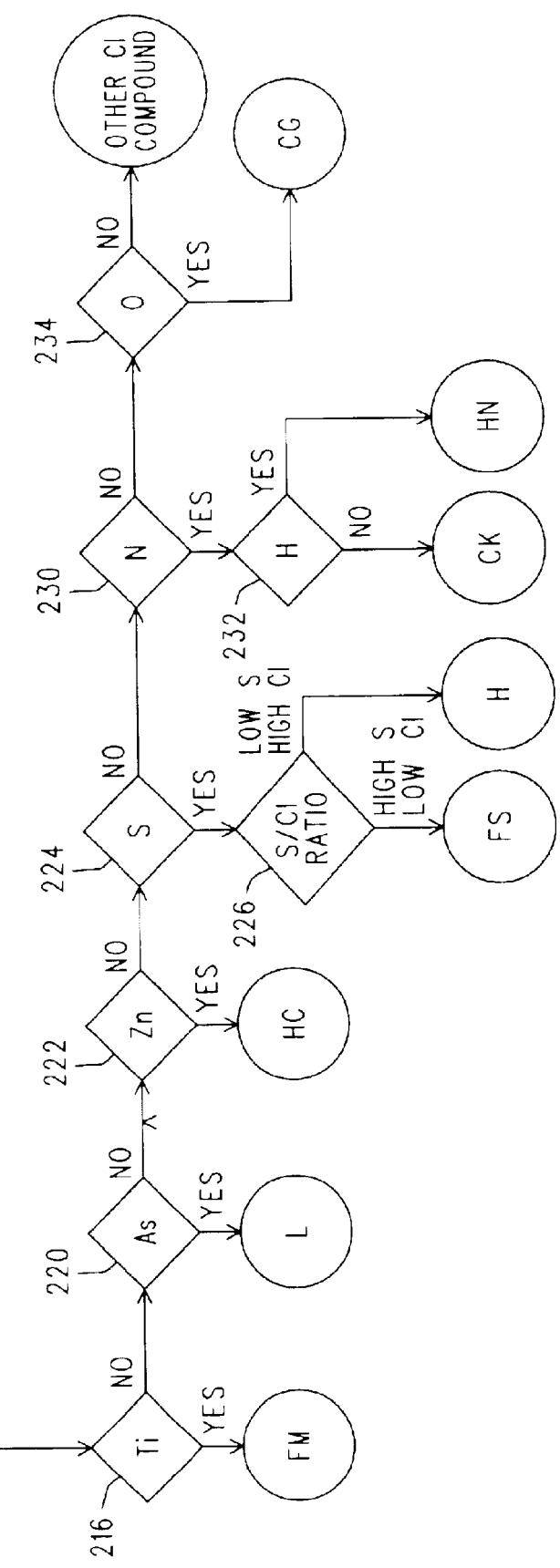

When the chemical elements are identified, a decision tree illustrated by the flow chart of FIGS. 9A and 9B is applied to the chemical elements. The decision tree will identify the agent 16 based on the chemical elements within the agent 16. It should be noted that the decision tree of FIGS. 9A and 9B is provided for example purposes only, is non-limiting in nature, and may be varied as needed.

Referring to FIGS. 1, 2, and the decision tree of FIGS. 9A and 9B, the element list is first queried at a step 200 for the presence of phosphorus. If the phosphorus content is sufficiently high relative to a predetermined value which is selected based on routine pilot testing, the computer 28 recognizes that the agent 16 in the munition 2 is white phosphorous smoke. The predetermined value may, as an example, correspond to greater than five counts per second in the 1266 keV phosphorus peak. The identification of the agent 16 may then be output via the screen 29 of the computer 28.

If phosphorous is not present or is present in low quantities, which again is predetermined and selected based on routine preliminary pilot testing, e.g., less than two counts per second in the 1266 keV phosphorus peak, a decision 202 is made to determine if chlorine is present in the agent 16. If there is little or no chlorine present, i.e., the 1950 keV chlorine net peak area is less than one-fourth the net peak area of the 2223 keV hydrogen peak, a decision 204 is made to determine if sulfur is present. If sulfur is present, a decision 206 is made to determine if phosphorous is also present in the agent 16. If phosphorus is present the presence of persistent nerve agent (VX) is reported to the operator. Referring to decision 204, if no sulfur is present, a decision 208 determines again if phosphorus is present. If phosphorus is present, the presence of nerve agent sarin (GB) is reported to the operator. If phosphorous was not detected at decision 208, a decision 210 is made to determine if nitrogen is present. If nitrogen is present, the presence of a high explosive (HE) is reported to the operator. Referring again to decision 210, if no nitrogen is present, a decision 212 is made to determine if boron is present. If boron is present, the presence of a water/antifreeze mixture is reported to the operator. If boron is not evident, a decision 214 is made to determine if silicon is present. If a high silicon to hydrogen ratio exists, the presence of sand is reported to the operator. The terms "high" and "low" with reference to the silicon (as well as other parameters expressed herein) ratio again relate to pre-selected values based on routine pilot testing. If none of the preceding elements are indicated in the spectrum, the computer 28 determines that the agent 16 is neither a high explosive nor a chemical warfare agent of the type recited above and listed in FIG. 9A.

Referring again to decision 202, if a high amount of chlorine is present, a decision 216 is made to determine if titanium is present. If titanium is present, then the agent 16 is determined to be FM smoke and this is reported to the operator. If no titanium is present, a decision 220 is made to determine if arsenic is present. If arsenic is present, then a lewisite is determined to be present and this is reported to the operator. If no arsenic is present, a decision 222 is made to determine if zinc is present. If zinc is present, then HC smoke is determined to be present in the agent 16 and this is reported to the operator. If no zinc is present, a decision 224 is made to determine if sulfur is present. If sulfur is present, a determination 226 of the sulfur to chlorine ratio is made at step 226. If the ratio is high, as determined and selected using routine preliminary pilot testing, the presence of FS smoke is reported to the operator. If the ratio is low, the presence of sulfur mustard gas (H) is reported to the operator.

Referring again to decision 224, if sulfur is not present, a decision 230 is made to determine if nitrogen is present in the agent 16. If nitrogen is present, a determination 232 is made to determine if hydrogen is also present. If hydrogen is not present, the presence of cyanogen chloride (CK) is reported to the operator. If hydrogen is also present, the presence of nitrogen mustard gas (HN) is reported to the operator.

Referring again to decision 230, if nitrogen is not present, a decision 234 is made to determine if oxygen is present. If oxygen is present, the presence of phosgene (CG) is reported to the operator. If no oxygen is present, a report is made to the operator that a compound other than those listed above and consisting of chlorine is present.

Referring again to FIGS. 1 and 2, during data acquisition using system 1, the spectrum may be displayed on the screen 29 of the computer 28. The operator monitors the spectrum to manually identify the chemical elements within the agent 16. To assist the operator, the computer 28 also identifies the chemical element producing each prominent gamma-ray peak in the spectrum.

Figure 10:
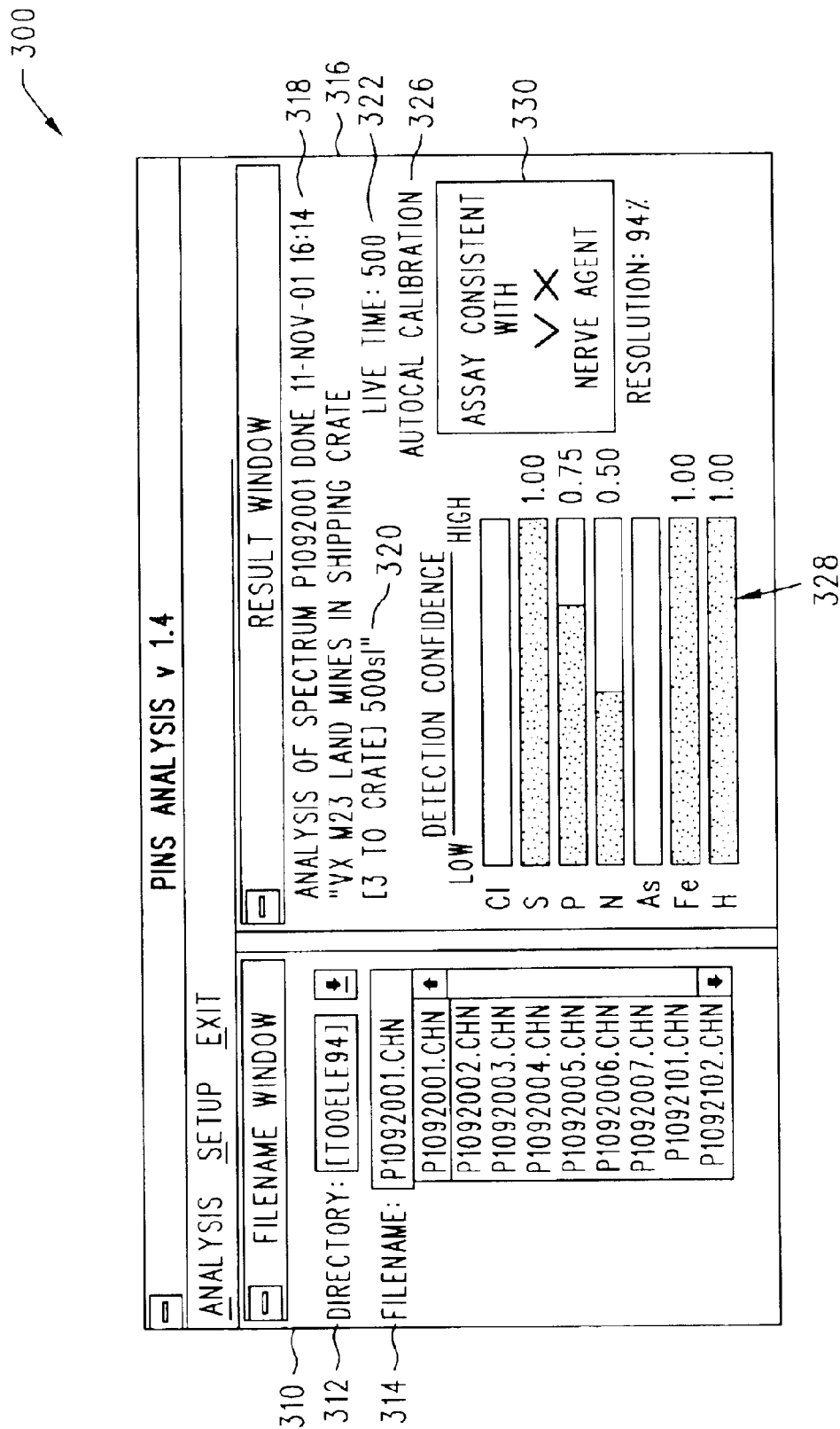
FIG. 10 is a display of a PINS analysis window for a spectrum of a VX-filled land mine using the computer of FIG. 1, with the term "VX" being defined below.

The above-described process of analyzing and identifying the agent 16 is performed by the computer 28. After data acquisition is complete, the operator can invoke an automatic spectrum analysis routine on the computer 28. This routine, after rechecking the energy calibration, identifies all of the gamma ray peaks in the spectrum, determines which chemical elements are present, and executes the decision tree logic described above and in FIGS. 9A and 9B to identify the agent 16 within the munition 2. FIG. 10 shows a non-limiting example of a display 300 generated by this routine on the computer screen 29. The spectrum analysis to be viewed is brought up in a file name window 310 within a directory 312 and having a file name 314.

A result window 316 identifies the spectrum number, acquisition date, and time at a location 318. Remarks about the munition being analyzed are reported at a location 320. The spectrum acquisition time is shown at a location 322 and the calibration method is shown at a location 326. The presence of chemical elements detected by the PINS assay and their respective detection confidence levels are reported on a bar chart 328. The identification of the agent is reported in readily readable form in a content box 330. For the display 300 shown in FIG. 10, the PINS assay was consistent with the presence of VX nerve agent in an M23 land mine.

Maintaining good energy resolution for the spectrum acquired by the system 1 is critical to accurate PINS assessment. Good energy resolution permits the identification of closely lying gamma-ray peaks of different chemical elements, and it also allows rejection of background peaks from various sources. Good energy resolution also reduces the counting time required to discern a weak peak from a strong background signal in a spectrum.

The energy resolution of a gamma-ray spectroscopy system can be degraded by insufficient detector cooling time, electronic gain shifts, noisy AC power, changes in the amplifier DC offset level, and excessive counting rates. Degraded energy resolution tends to broaden the gamma ray peaks and reduce their amplitudes.

Figure 11:
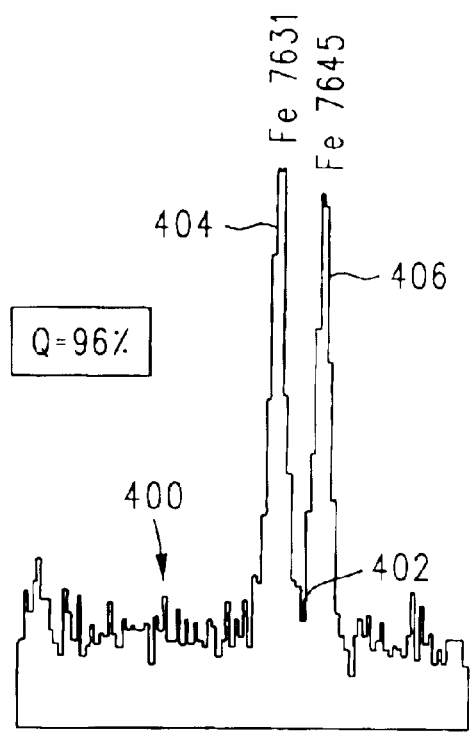
FIG. 11 shows the 7,631 and 7,645 keV peaks of a gamma-ray spectrum of iron having good resolution.
Figure 12:
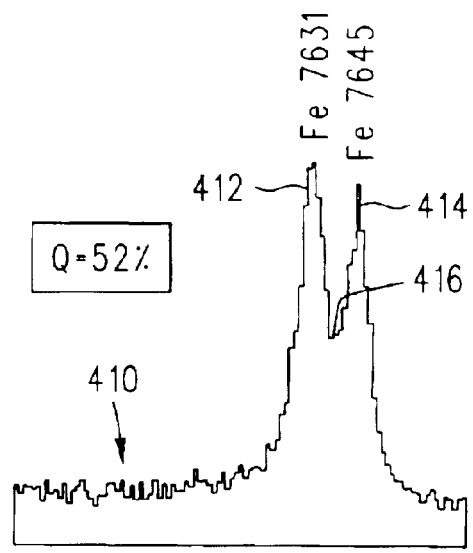
FIG. 12 shows the 7,631 and 7,645 keV peaks of a gamma-ray spectrum of iron having relatively poor resolution.

With reference to FIGS. 11 and 12, to maintain good energy resolution, the operator of system 1 monitors the 7.6 MeV iron doublet peak-to-valley ratio. The spectrum 400 shown in FIG. 11 exhibits a deep valley 402 between the iron peak 404 at 7.631 MeV and the iron peak 406 at 7.645 MeV. The presence of deep valley 402 indicates good energy resolution. The iron spectrum 410 of FIG. 12 shows the 7.631 MeV peak 412 and the 7.645 MeV peak 414 with a less-defined valley 416 between them. If a spectrum similar to that shown in FIG. 12 is displayed on the computer 28, the system operator makes adjustments to improve energy resolution. The spectrum quality index, Q, for the iron doublets of FIGS. 11 and 12 are reported on the screen 29 of the computer 28. The value of Q is determined by subtracting the number of net or background-subtracted valley counts divided by the number of net peak counts from 1 and multiplying by 100. If the value of Q falls below 70 percent, it is recommended that the operator repeats the measurement.

Figure 13:
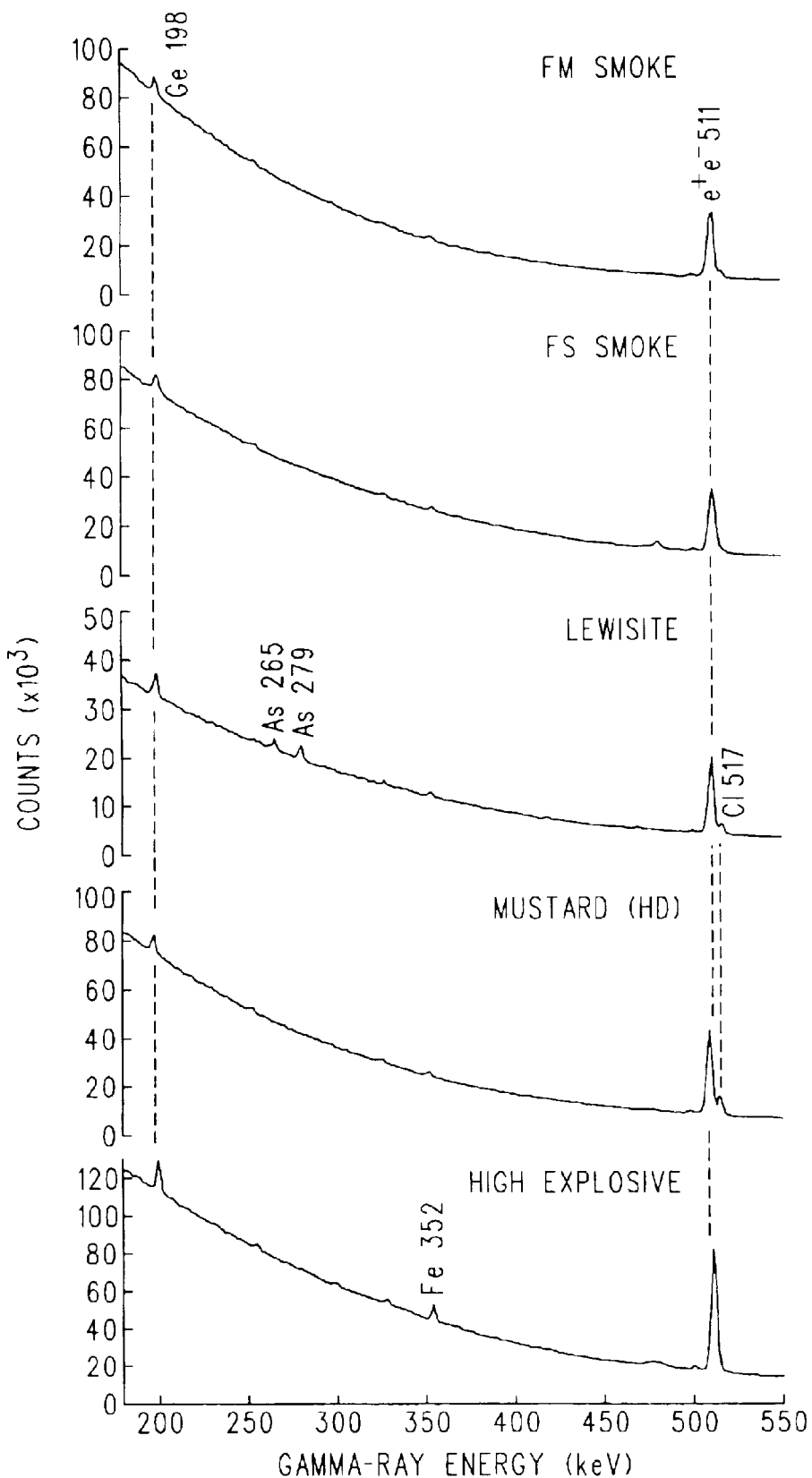
FIGS. 13 and 14 show the 200 to 550 keV gamma-ray spectra regions for a number of military agents, practice fills, and sand including the 511 keV peak that results from the annihilation of positron-electron pairs that is used for calibration purposes.
Figure 14:
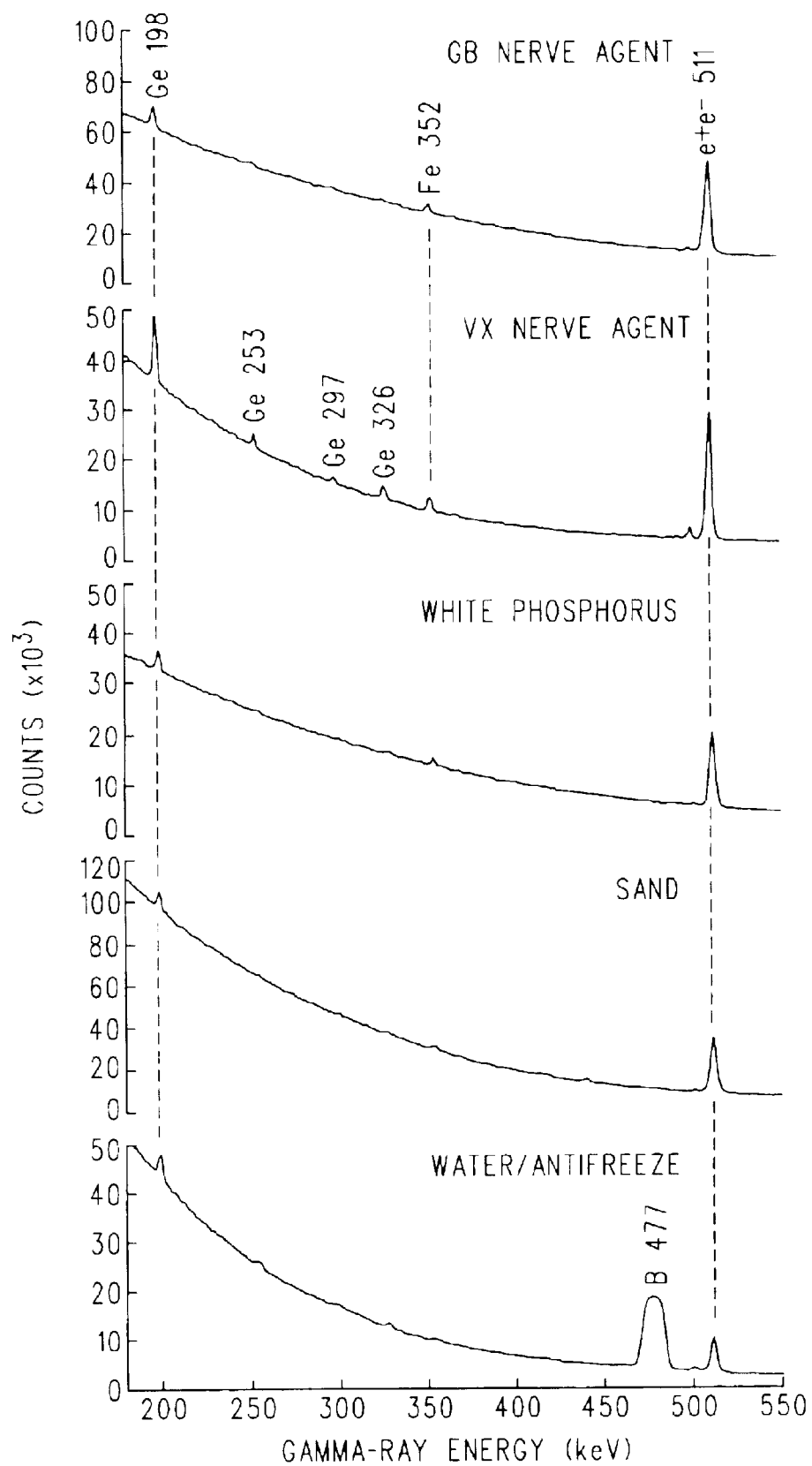
Figure 15:
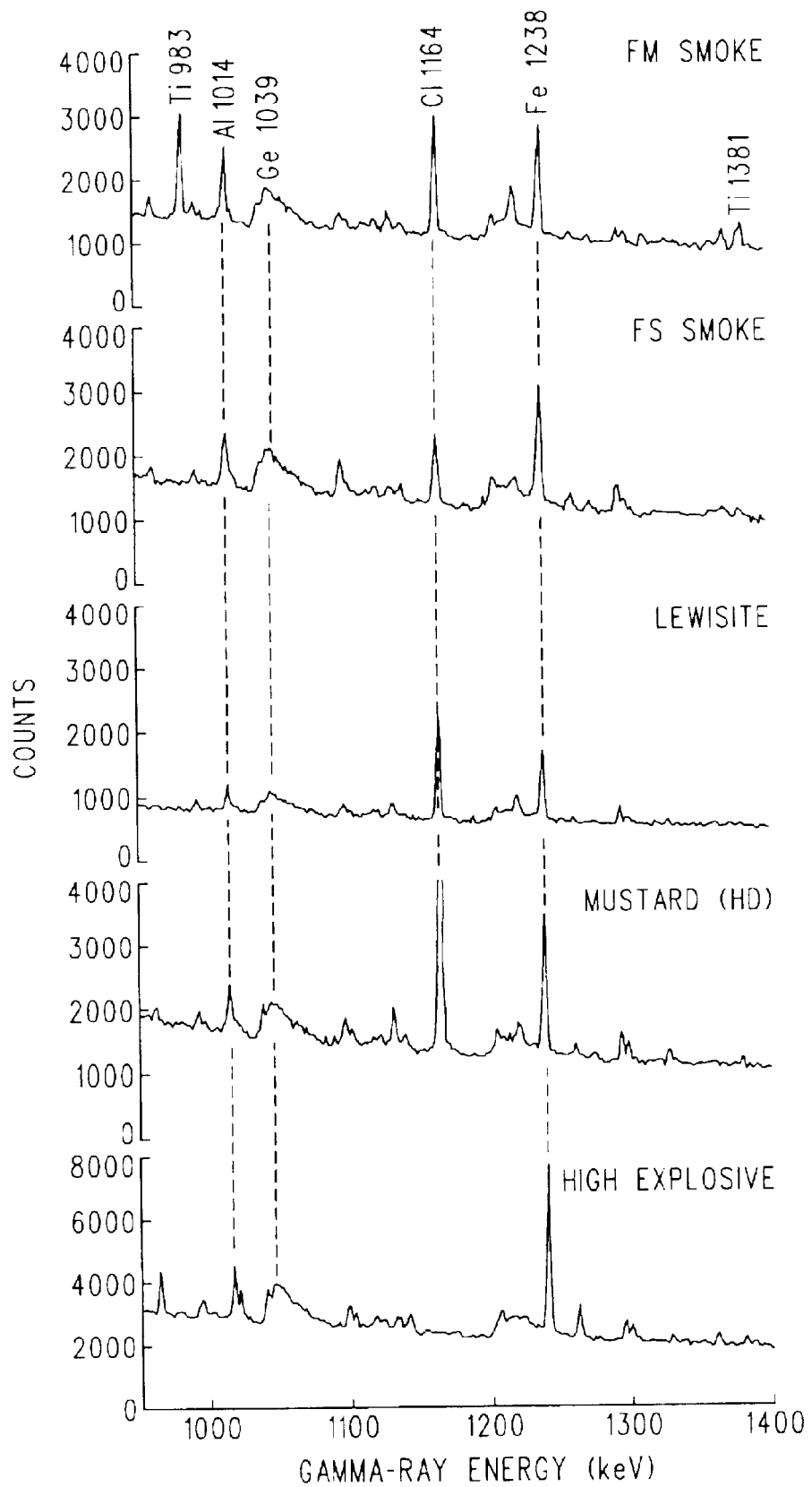
FIGS. 15 and 16 show the PINS phosphorous region of the gamma-ray spectra between about 900 and 1,400 keV for the military fills of FIGS. 13 and 14.
Figure 16:
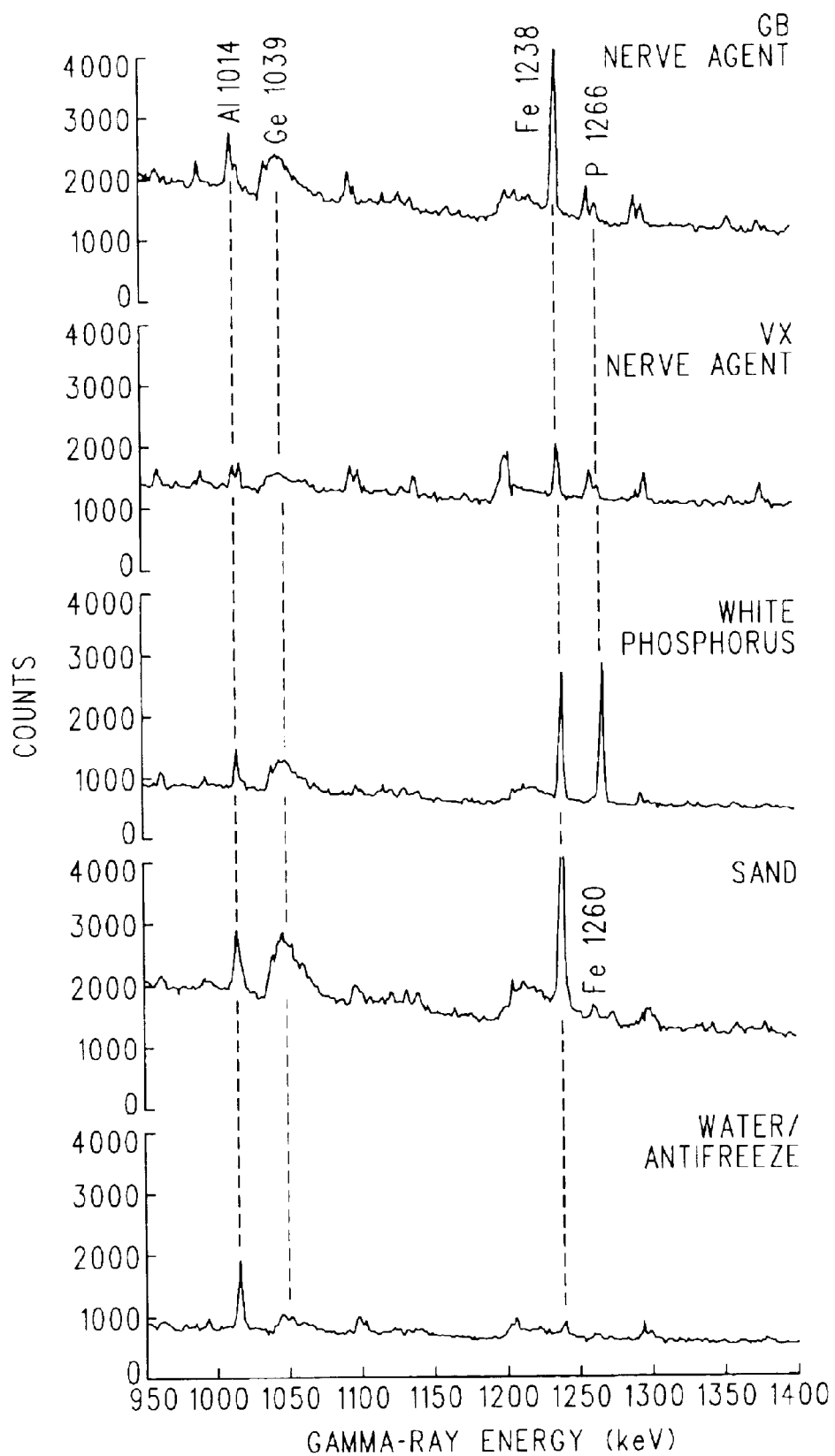
Figure 17:
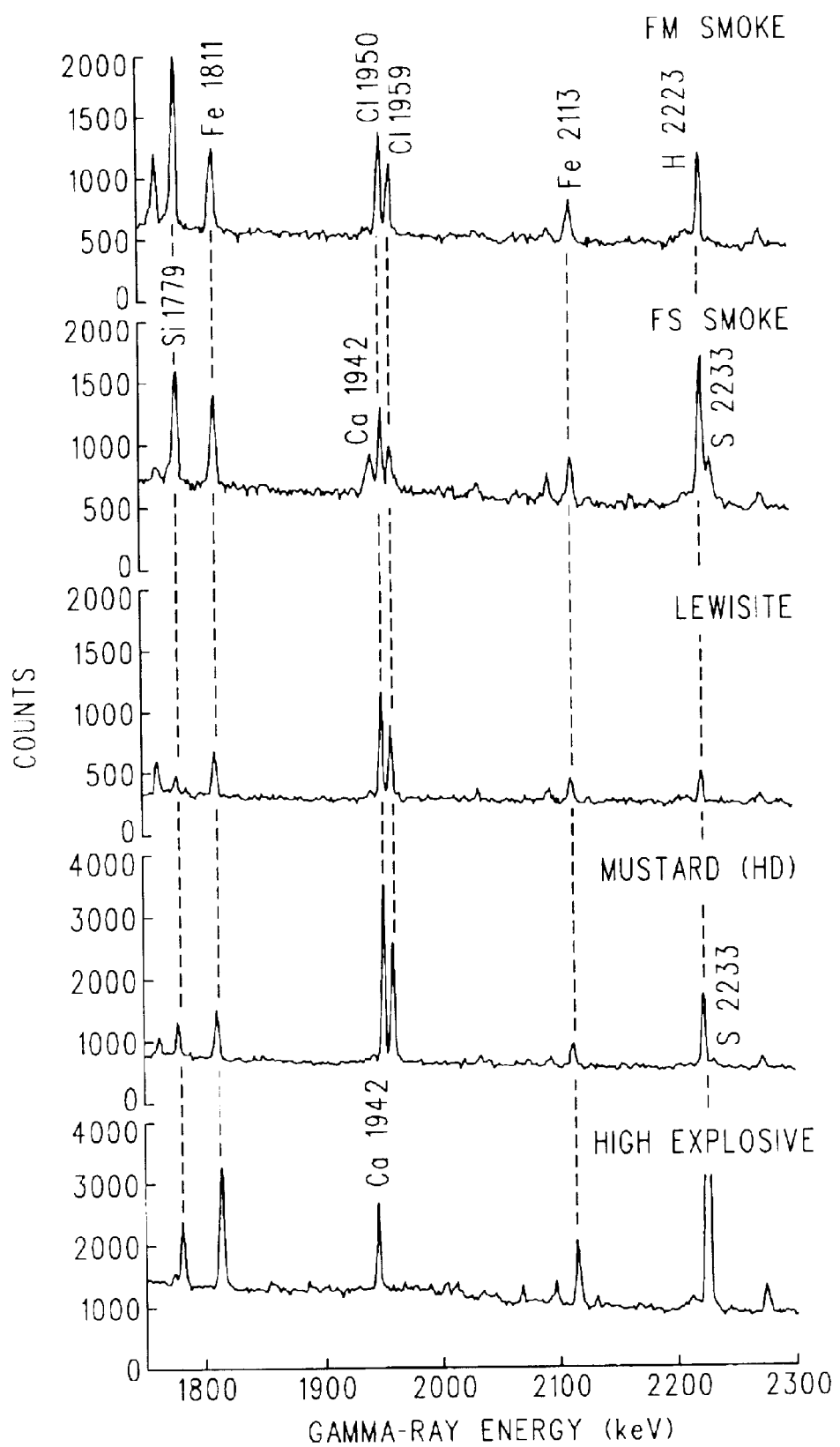
FIGS. 17 and 18 show the PINS hydrogen region of the gamma-ray spectra between about 1,500 and 2,300 keV for the military fills of FIGS. 13 and 14.
Figure 18:
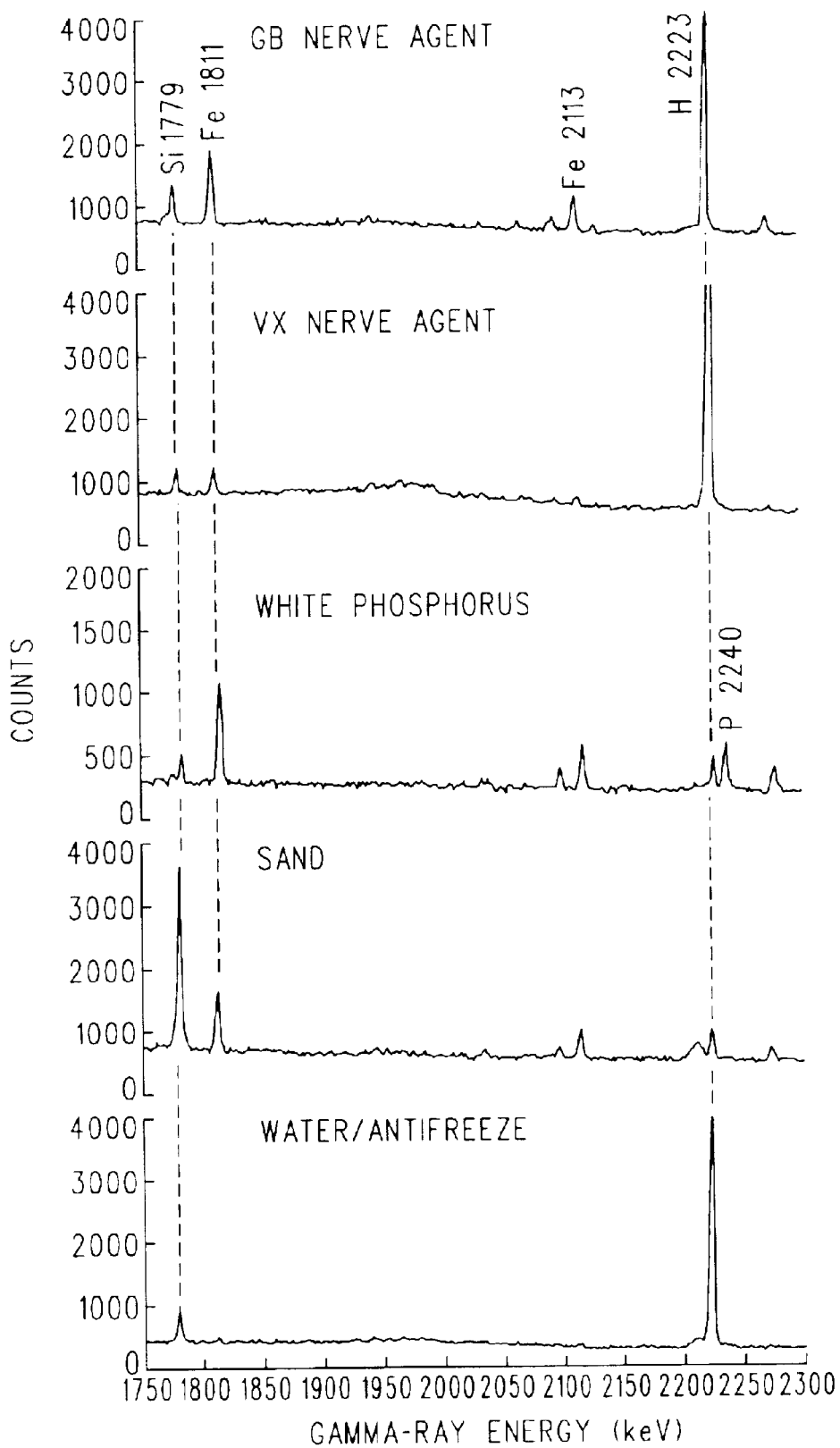
Figure 19:
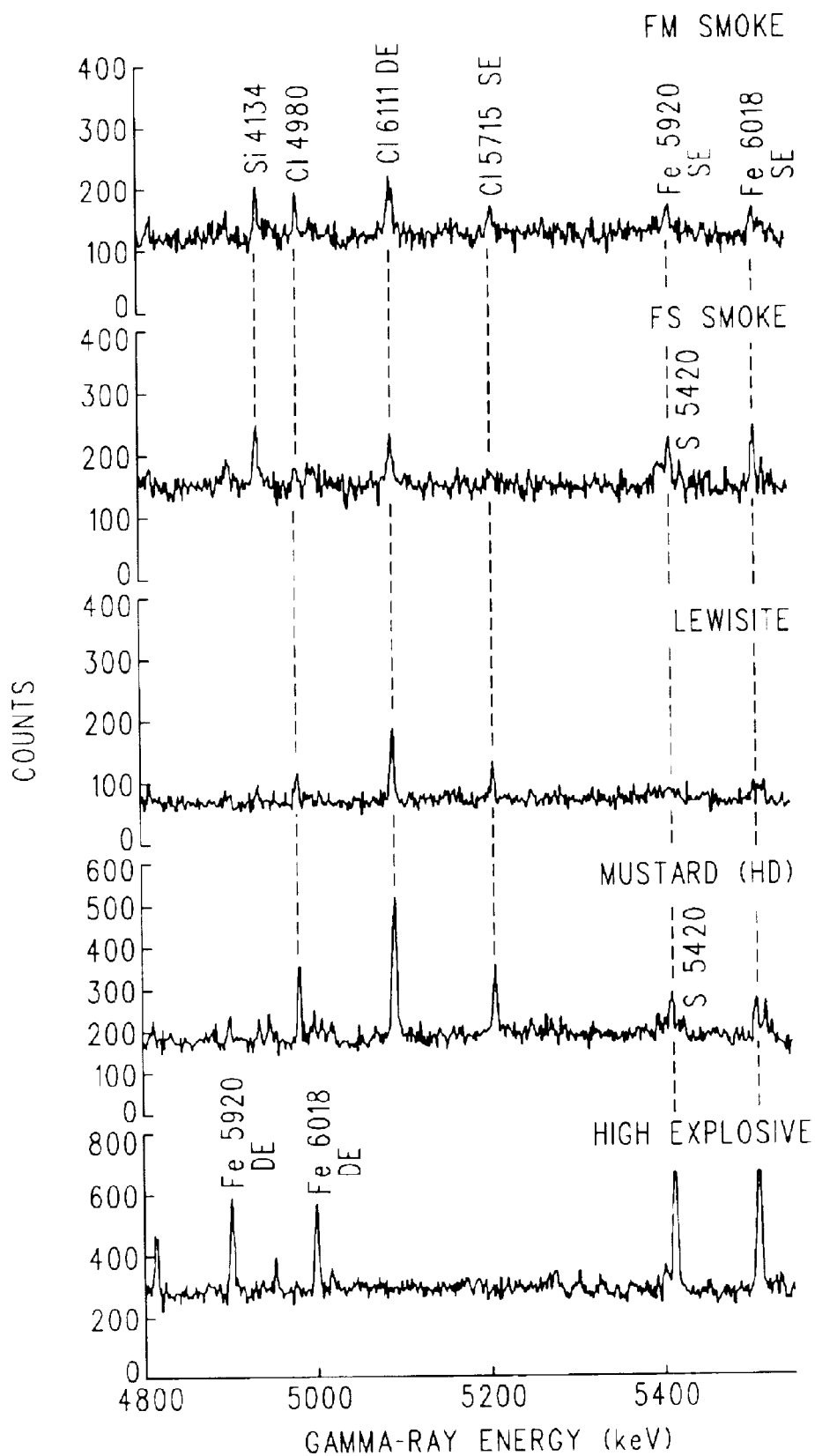
FIGS. 19 and 20 show the PINS sulfur region of the gamma-ray spectra between about 4,800 and 5,400 keV for the military fills of FIGS. 13 and 14.
Figure 20:
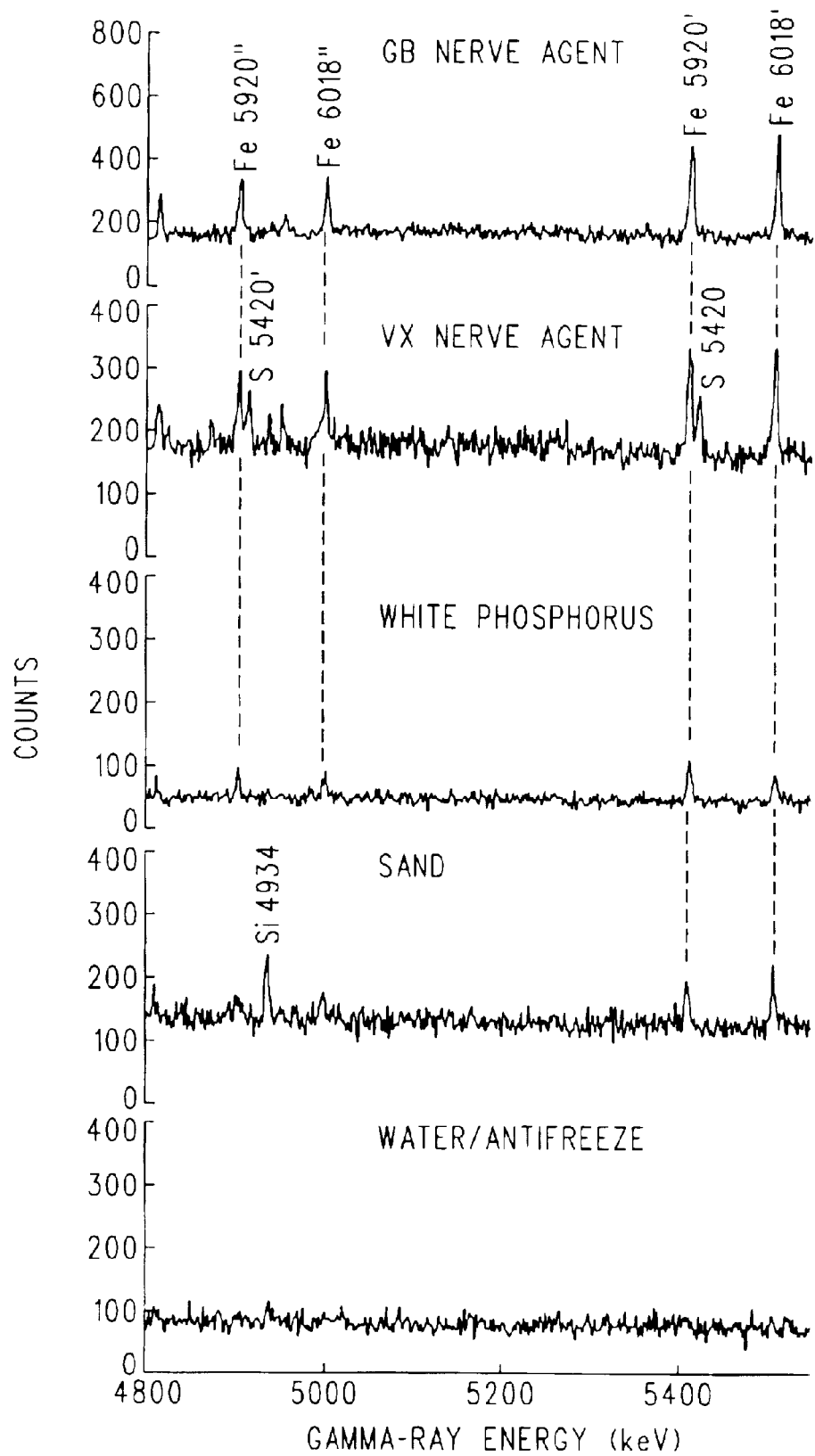
Figure 21:
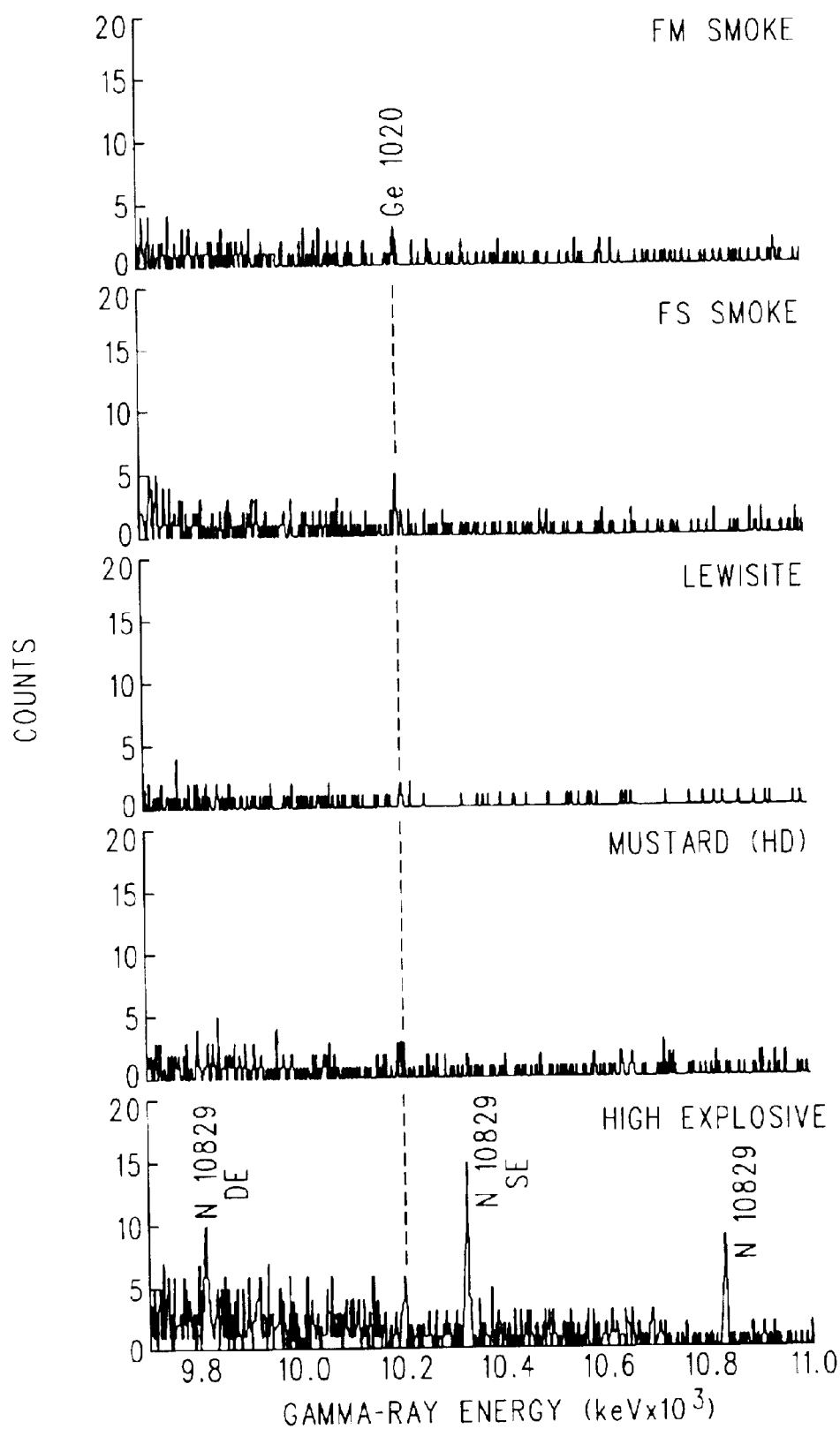
FIGS. 21 and 22 show the PINS nitrogen region of the gamma-ray spectra between about 9,800 and 11,000 keV for the military fills of FIGS. 13 and 14.
Figure 22:
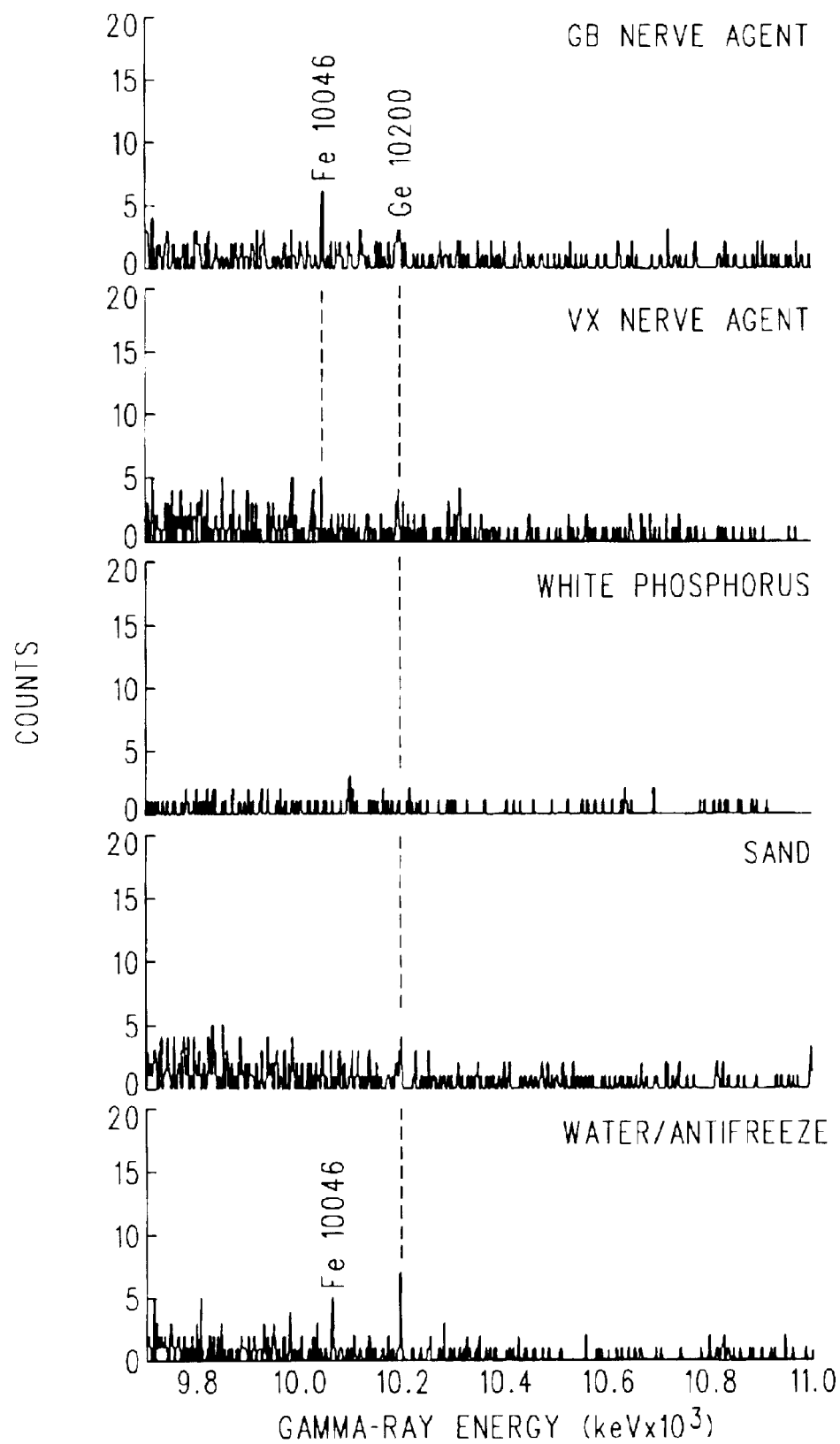

FIGS. 13 through 22 contain example spectra for ten of the most common military munition fills of field-recovered munitions and containers assessed using the subject method and apparatus. FIGS. 13 and 14 show spectra in the arsenic region, FIGS. 15 and 16 show spectra in the phosphorus region. FIGS. 17 and 18 show spectra in the hydrogen region. FIGS. 19 and 20 show spectra in the sulfur region. FIGS. 21 and 22 show spectra in the nitrogen region. Each two-figure region of interest displays ten spectra, each spectrum for a different fill, grouped by common key elements for purposes of visual comparison. Four fills containing chlorine appear first, followed by high explosive, then three fills that contain phosphorus, and finally two simulant fills, i.e., sand and water The system 1 has been described herein as being able to identify agents present within munitions. It is to be understood that the system and apparatus may be adapted to identify other chemical elements or agents present in other types of containers. In addition, the system 1 may be adapted to identify agents that are not located within containers.

The system 1, FIG. 1, has been described has providing a confidence to the user. The confidence may be calculated as described below. For each element the peak fit results for each of the peaks of the particular element are found. A confidence array, conf_array, for the element is created to categorize the peaks found (nominally with 5 elements). The conf_array is then initialized to all zeros (e.g. conf_array [0,0,0,0,0]). Next, the quality of each peak of the element is determined by using an algorithm similar to "cat=int (uncertainty/20))". For this non-limiting example, it is assumed that there are four peaks for the element sulfur, and their uncertainties were 18%, 55%, 8%, and 85%.

For each of these peaks, the conf_array array element corresponding to the peak quality level is incremented. Therefore, the best peaks (uncertainty close to zero) will cause the first element in the array to be incremented. In this example, the first peak (18% uncertainty) causes the first element in the conf_array to be incremented (then, conf_array would contain [1,0,0,0,0]). The next 3 peaks cause the $3^{rd}$, $1^{st}$, and $4^{th}$ elements respectively to be incremented (conf_array will now contain [2,0,1,1,0]).

After all the peaks from the element have been processed, the conf_array is used to determine the overall confidence of that element. This is accomplished by a confidence table being created for each element. The table contains a series of conf_array values that must be met or exceeded to meet that confidence level. For example, to achieve a 50% confidence level, 2 peaks with 20% or less error along with 3 peaks of 60% or less error may be required (e.g. (2,0,1,0,0)). There are approximately 7 distinct table entries that are checked against the conf_array values. The first one that is met or exceeded determines the overall confidence measure for that element. A confidence level is assigned to each of the table entries in the confidence table and the highest level met or exceeded is used in reporting the confidence of the element. For example, if the conf_array is [2,0,1,1,0] as described above, and the confidence table is [[4,0,0,0,0], [3,1,0,0,0], [1,1,1,0,0], [0,1,2,0,0], [0,0,3,0,0], [0,0,2,1,0], [0,0,1,2,0]], then the third confidence level would be met [1, 1,1,0,0]. At a minimum, one peak with less than 20% uncertainty, an additional peak with less than 40% uncertainty, and a third peak with less than a 60% uncertainty).

A confidence value is then given to the element based on a lookup table that pairs a value to each confidence level achieved. Usually the confidence values assigned pair the first level with 100%, $2^{nd}$ with 75%, third with 50% fourth with 25%, $5^{th}$ with 10%, $6^{th}$ with 5%, and $7^{th}$ with 0%. In this example, the $3^{rd}$ element of the confidence table was met which will correspond to an overall confidence of 50% based on the lookup table value.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method for identifying a chemical substance, the method comprising:

exposing said chemical substance to neutrons from an isotopic neutron source;

measuring, with a high purity germanium detector, gamma rays emitted by said chemical substance as a result of exposure to said neutrons;

creating a single spectrum of between 4096 and 16384 channels and a detection count per spectrum channel, said detection count corresponding to the number of detected gamma rays;

calibrating from said single spectrum, an energy scale based on energies within said single spectrum of neutron-induced gamma rays generated from said detector, shielding materials or container materials;

performing a peak-by-peak analysis of the corresponding gamma-ray energies of chemical elements of interest on said spectrum; and identifying said chemical substance based on said peak-by-peak analysis of said single spectrum.

2. The method of claim 1 further comprising displaying chemical elements comprising said identified chemical substance.

3. The method of claim 2 further comprising displaying a confidence level associated with the identified chemical elements.

4. The method of claim 1 further comprising displaying the identified chemical substance.

5. The method of claim 1 further comprising displaying a confidence level associated with the identified chemical substance.

6. The method of claim 1 wherein the step of identifying the chemical substance comprises determining a presence, if any, of a first chemical element selected from the group of phosphorous and chlorine, and a ratio of second elements selected from the group consisting of arsenic, boron, hydrogen, nitrogen, oxygen, phosphorous, sulfur, silicon, titanium and zinc.

7. The method of claim 1 further comprising a step of calibrating an electronic gain of said high purity detector to adjust a known gamma-ray peak to a pre-selected channel of said high purity detector.

8. The method of claim 7 wherein said known gamma-ray peak is associated with hydrogen.

9. The method of claim 8 wherein said known gamma-ray peak associated with hydrogen is generated from neutron interactions within a hydrogenous moderator block.

10. The method of claim 9 wherein the moderator block comprises polyethylene.

11. A method for identifying a chemical substance, the method comprising:
    inducing neutrons from an isotopic neutron source into a chemical substance, said neutrons interacting within the chemical substance to generate characteristic gamma-rays;
    measuring, with a high purity germanium detector, energies of said gamma-rays to create a single gamma-ray energy spectrum;
    calibrating from said single spectrum, an energy scale based upon energies within said single spectrum of neutron-induced gamma rays generated from said detector, shielding materials or container materials;
    performing a directed peak fit analysis comprising determining peak centroids and net peak areas extracted from said calibrated, single spectrum to determine gamma-ray counting rates for chemical elements of interest;
    identifying chemical elements and their ratios contained in said chemical substance;
    identifying said chemical substance by determining a presence, if any, of a first clement and at least one second element.

12. The method of claim 11 wherein said first element concentration is selected from the group consisting of phosphorous and chlorine.

13. The method of claim 11 wherein said at least one second element concentration is selected from the group consisting of arsenic, boron, hydrogen, nitrogen, oxygen, phosphorous, sulfur, silicon, titanium and zinc.

14. The method of claim 11 further comprising the step of calibrating an electronic gain of said high purity detector to adjust a known gamma-ray peak to a pre-selected channel of said high purity detector.

15. The method of claim 14 wherein said known gamma-ray peak is associated with hydrogen.

16. The method of claim 15 wherein said known gamma-ray peak associated with hydrogen is generated from neutron interactions within a hydrogenous moderator block.

17. The method of claim 16 wherein the moderator block comprises polyethylene.

18. The method of claim 11 wherein data file information of at least one known chemical element and gamma-ray peaks associated therewith is selected from the group consisting of iron and chlorine.

19. The method of claim 11 wherein data information of known chemical elements and gamma-ray peaks associated therewith is comprised of elements contained within said detector, shielding materials or container materials.

20. The method of claim 19 wherein said data information of known chemical elements is selected from the group consisting of germanium, bismuth, aluminum, and iron.

21. The method of claim 11 further comprising displaying the identified chemical elements.

22. The method of claim 11 further comprising displaying the identified chemical substance.

23. The method of claim 11 further comprising displaying a confidence level associated with the identified chemical elements.

24. The method of claim 11 further comprising displaying a confidence level associated with the identified chemical substance.

* * * * *